US008853274B1

United States Patent
Wang

(10) Patent No.: US 8,853,274 B1
(45) Date of Patent: Oct. 7, 2014

(54) COMPOSITIONS AND METHODS FOR TARGETING GLIOBLASTOMAS CELLS

(75) Inventor: Jialiang Wang, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 156 days.

(21) Appl. No.: 13/617,486

(22) Filed: Sep. 14, 2012

Related U.S. Application Data

(60) Provisional application No. 61/534,646, filed on Sep. 14, 2011.

(51) Int. Cl.
| | |
|---|---|
| *A01N 37/44* | (2006.01) |
| *A61K 31/195* | (2006.01) |
| *A61K 31/235* | (2006.01) |
| *A61K 31/4545* | (2006.01) |
| *A61K 31/223* | (2006.01) |
| *A61K 31/4709* | (2006.01) |
| *A61K 31/5513* | (2006.01) |
| *A61K 31/55* | (2006.01) |

(52) U.S. Cl.
CPC ............. *A61K 31/55* (2013.01); *A61K 31/4545* (2013.01); *A61K 31/223* (2013.01); *A61K 31/4709* (2013.01); *A61K 31/5513* (2013.01)
USPC ............................ 514/562; 514/479; 514/542

(58) Field of Classification Search
CPC . A61K 2300/00; A61K 31/216; A61K 31/27; A61K 31/713; A61K 41/0038
USPC .......................................... 514/479, 542, 562
See application file for complete search history.

(56) References Cited

PUBLICATIONS

Lo, H.-W., "Targeting Ras-RAF-ERK and its Interactive Pathways as a Novel Therapy for Malignant Gliomas", 2010, Current Cancer Drug Targets, 10(8), pp. 840-848.*
Schreck et al., "The Notch Target Hes1 Directly Modulates Gli1 Expression and Hedgehog Signaling: A Potential Mechanism of Therapeutic Resistance", 2010, Clin Cancer Res, 16(24), pp. 6060-6070.*
Porzner et al., "Novel Approaches to Target Pancreatic Cancer", 2011, Current Cancer Drug Targets, 11(6), pp. 698-713.*
Samon et al., "Preclinical Analysis of the g-Secretase Inhibitor PF-03084014 in Combination with Glucocorticoids in T-cell Acute Lymphoblastic Leukemia", 2012, Mol Cancer Ther, 11(7), pp. 1565-1575.*
Bao S, Wu Q, McLendon RE, Hao Y, Shi Q, Hjelmeland AB, et al. Glioma stem cells promote radioresistance by preferential activation of the DNA damage response. Nature. 2006;444(7120):756-60.
Wang J, Wakeman TP, Lathia JD, Hjelmeland AB, Wang X-F, White RR, et al. Notch Promotes Radioresistance of Glioma Stem Cells. Stem Cells. 2010;28(1):17-28.
Hambardzumyan D, Squatrito M, Holland EC. Radiation resistance and stem-like cells in brain tumors. Cancer Cell. 2006;10(6):454-6.
Pannuti A, Foreman K, Rizzo P, Osipo C, Golde T, Osborne B, et al. Targeting Notch to target cancer stem cells. Clin Cancer Res. 2010;16(12):3141-52.
Phillips TM, McBride WH, Pajonk F. The repsonse of CD24(-/low)/CD44+ breast cancer-initiating cells to radiation. J Natl Cancer Inst. 2006;98:1777-85.
Diehn M, CHo RW, Lobo NA, Kalisky T, Dorie MJ, Kulp AN, et al. Association of reactive oxygen species levels and radioresistance in cancer stem cells. Nature. 2009; 458:890-3.
Hoey T, Yen WC, Axelrod F, Basi J, Donigian L, Dylia S, et al. DLL4 blockade inhibits tumor growth and reduces tumor-initiating cell frequency. Cell Stem Cell. 2009;5:168-77.
Gilbert CA, Daou MC, Moser RP, Ross AH. Gamma-secretase inhibitors enhance temozolomide treatment of human gliomas by inhibiting neurosphere repopulation and xenograft recurrence. Cancer Res. 2010;70(17):6870-9.
Fan X, Khaki L, Zhu TS, Soules ME, Talsma CE, Gul N, et al. Notch pathway blockade depletes CD133-positive glioblastoma cells and inhibits growth of tumor neurospheres and xenografts. Stem Cells. 2010;28(1):5-16.
Fan X, Matsui W, Khaki L, Stearns D, Chun J, Li YM, et al. Notch pathway inhibition depletes stem-like cells and blocks engraftment in embryonal brain tumors. Cancer Res. 2006;66(15):7445-52.
Chen J, Kesari S, Rooney C, Strack PR, Shen H, Wu L, et al. Inhibition of Notch Signaling Blocks Growth of Glioblastoma Cell Lines and Tumor Neurospheres. Genes Cancer. 2010;1(8):822-35.
Liu A, Cemiglia GJ, Bernhard EJ, Prendergast GC. RhoB is required to mediate apoptosis in neoplastically transformed cells after DNA damage. Proc Natl Acad Sci U S A. 2001;98(11):6192-7.
Cloughesy TF, Kuhn J, Robins HI, Abrey L, Wen P, Fink K, et al. Phase I trial of tipifarnib in patients with recurrent malignant glioma taking enzyme-inducing antiepileptic drugs: a North American Brain Tumor Consortium Study. J Clin Oncol. 2005;23(27):6647-56.
Cloughesy TF, Wen PY, Robins HI, Chang SM, Groves MD, Fink KL, et al. Phase II trial of tipifarnib in patients with recurrent malignant glioma either receiving or not receiving enzyme-inducing antiepileptic drugs: a North American Brain Tumor Consortium Study. J Clin Oncol. 2006;24(22):3651-6.

(Continued)

*Primary Examiner* — My-Chau T Tran
(74) *Attorney, Agent, or Firm* — Stites & Harbison PLLC; Mandy Wilson Decker

(57) ABSTRACT

A composition including a farnesyl transferase inhibitor (FTI) and a gamma-secretase inhibitor (GSI) is useful for producing an effect against a glioblastoma cell and/or for treating glioblastoma multiforme (GBM).

24 Claims, 8 Drawing Sheets

(56) References Cited

PUBLICATIONS

Haas-Kogan DA, Banerjee A, Kocak M, Prados MD, Geyer JR, Fouladi M, et al. Phase I trial of tipifarnib in children with newly diagnosed intrinsic diffuse brainstem glioma. Neuro Oncol. 2008;10:341-7.

Haas-Kogan DA, Banerjee A, Poussaint TY, Kocak M, Prados MD, Geyer Jr, et al. Phase II trial of tipifarnib and radiation in children with newly diagnosed diffuse intrinsic pontine gliomas. Neuro Oncol. 2011;13(3):298-306. PMCID:3064607.

Lee J, Kotliarova S, Kotliarov Y, Li A, Su Q, Donin NM, et al. Tumor stem cells derived from glioblastomas cultured in bFGF and EGF more closely mirror the phenotype and genotype of primary tumors than do serum-cultured cell lines. Cancer Cell. 2006;9(5):391-403.

Weijzen S, Rizzo P, Braid M, Vaishnav R, Jonkheer SM, Zlobin A, et al. Activation of Notch-1 signaling maintains the neoplastic phenotype in human RAS-transformed cells. Nat Med. 2002;8(9):979-86.

Dong Y, Li A, Wang J, Weber JD, Michel LS. Synthetic lethality through combined Notch-epidermal growth factor receptor pathway inhibition in basal-like breast cancer. Cancer Res. 2010;70(13):5465-74.

Luistro L, He W, Smith M, Packman K, Vilenchik M, Carvajal D, et al. Preclinical profile of a potent gamma-secretase inhibitor targeting notch signaling with in vivo efficacy and pharmacodynamic properties. Cancer Res. 2009;69 (19):7672-80.

Krop I, Demuth T, Guthrie T, Wen PY, Mason WP, Chinnalyan P, et al. Phase I Pharmacologic and Pharmacodynamic Study of the Gamma Secretase (Notch) inhibitor MK-0752 in Adult Patients With Advanced Solid Tumors. J Clin Oncol. 2012.

Strosberg JR, Yeatman T, Weber J, Coppola D, Schell MJ, Han G, et al. A phase II study of RO4929097 in metastatic colorectal cancer. Eur J Cancer. 2012; 48:997-1003.

Tolcher AW, Messersmith WA, Mikulski SM, Papadopoulos KP, Kwak EL, Gibbon DG, et al. Phase I Study of RO4929097, a Gamma Secretase Inhibitor of Notch Signaling, in Patients With Refractory Metastatic or Locally Advanced Solid Tumors. J Clin Oncol. 2012.

\* cited by examiner

COMPOSITIONS AND METHODS FOR TARGETING GLIOBLASTOMAS CELLS

RELATED APPLICATIONS

This application claims priority from U.S. Provisional Application Ser. No. 61/534,646 filed Sep. 14, 2011, the entire disclosure of which is incorporated herein by this reference.

TECHNICAL FIELD

The presently-disclosed subject matter relates to treatment for glioblastoma. In particular, the presently-disclosed subject matter relates to compositions and methods having unexpectedly superior efficacy for inhibiting growth of and/or killing glioblastoma cells.

INTRODUCTION

Glioblastoma multiforme (GBM) is among the most lethal human tumors with an average survival of about 14 months following diagnosis. Maximal surgical resection of the tumor mass followed by radiation and chemotherapy is the current standard of care. GBM may initially respond to chemoradiotherapy, however, subsequent local recurrence is universal. Until recently, there was a lack of mechanistic understanding for this observation. Emerging research suggests that cancer stem cells (CSCs) may represent a significant driving force underlying radiation resistance and tumor recurrence in GBM (Diehn, et al., 2009). GBM stem cells (GSCs) appear to be more resistant to radiation than matched non-stem tumor cells (Bao, et al., 2006), suggesting that they are important targets to investigate the mechanistic connections between GBM radioresistance and clinical outcomes. Although progress has been made toward understanding the role of GSCs in radiotherapy, there is a considerable gap in knowledge regarding the signaling networks responsible for radiation failure. There is also a lack of known radiosensitizers that may effectively compromise the radioresistant phenotype of GSCs.

Accordingly, there remains a need in the art for effective compositions and methods for targeting glioblastoma cells.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes compositions and methods for targeting or producing an effect against a glioblastoma cells, including glioblastoma multiform (GBM) stem cells. Compositions and methods of the presently-disclosed subject matter can have utility in the treatment of glioblastoma multiforme (GBM). Compositions of the presently-disclosed subject matter include a farnesyl transferase inhibitor (FTI), and a gamma secretase inhibitor (GSI). In some embodiments, the compositions are pharmaceutical compositions.

In some embodiments, wherein the FTI is selected from tipifarnib and L744,832. In some embodiments, the FTI is tipifarnib. In some embodiments, the FTI is L744,832. In some embodiments, the GSI is selected from RO4929097, DAPT, and compound E. In some embodiments, the GSI is RO4929097. In some embodiments, the GSI is DAPT. In some embodiments, the GSI is compound E.

In some embodiments, the FTI is selected from tipifarnib and L744,832; and the GSI is selected from RO4929097, DAPT, and compound E. In some embodiments, the FTI is tipifarnib and the GSI is RO4929097. In some embodiments, the FTI is L744,832 and the GSI is DAPT.

In some embodiments, the FTI and GSI are provided in a ratio selected from about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20 (wt/wt).

In some embodiments, the composition is provided for the treatment of glioblastoma multiforme (GBM). In some embodiments, the combination produces an effect against glioblastoma cells. In some embodiments, the effect against glioblastoma cells is selected from an inhibition in the growth of glioblastoma cells, a killing of glioblastoma cells, and a reduction in symptoms associated with the presence of glioblastoma cells. In some embodiments, the combination of the FTI and the GSI produce a synergistic effect against glioblastoma cells.

Methods of the presently-disclosed subject matter include contacting a glioblastoma cell with a composition, comprising a farnesyl transferase inhibitor (FTI); and a gamma-secretase inhibitor (GSI). In some embodiments, contacting a glioblastoma cell with the composition comprises administering the composition to a subject. In some embodiments, methods of the presently-disclosed subject matter include administering an effective amount of a composition comprising a farnesyl transferase inhibitor (FTI) and a gamma secretase inhibitor (GSI) to a subject. In some embodiments, the method can further include administering radiation, wherein the administration of the composition increases the sensitivity of the cells to the radiation. The presently-disclosed subject matter includes use of the compositions disclosed herein for the treatment of glioblastoma multiforme (GBM).

In some embodiments, methods produce an effect against glioblastoma cells, selected from an inhibition in the growth of glioblastoma cells, a killing of glioblastoma cells, and a reduction in symptoms associated with the presence of glioblastoma cells.

In some embodiments, the combination of the FTI and the GSI produce a synergistic effect against the glioblastoma cell. In some embodiments, the effect against glioblastoma cells is selected from an inhibition in the growth of glioblastoma cells, a killing of glioblastoma cells, and a reduction in symptoms associated with the presence of glioblastoma cells.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

DESCRIPTION OF EXEMPLARY EMBODIMENTS

Figure 1:
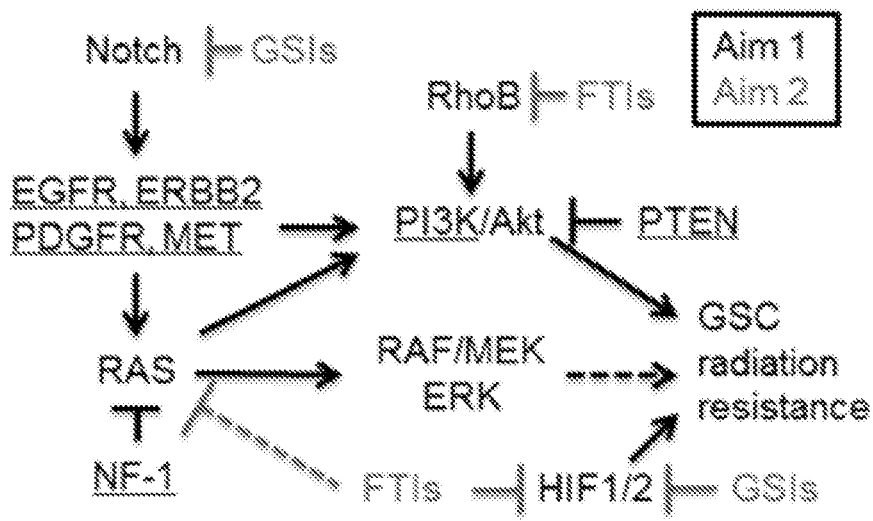
FIG. 1 is a flow chart showing the contemplated role of Notch in regulating a pro-survival signaling network in GSCs.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes compositions and methods for targeting or producing an effect against a glioblastoma cells, including glioblastoma multiform (GBM) stem cells. Compositions and methods of the presently-disclosed subject matter can have utility in the treatment of gliblastoma multiforme (GBM). Compositions of the presently-disclosed subject matter include a farnesyl transferase inhibitor (FTI), and a gamma secretase inhibitor (GSI). In some embodiments, the compositions are pharmaceutical compositions. Methods of the presently-disclosed subject matter include administering an effective amount of a composition comprising a farnesyl transferase inhibitor (FTI) and a gamma secretase inhibitor (GSI) to a subject. In some embodiments, the method can further include administering radiation, wherein the administration of the composition increases the sensitivity of the cells to the radiation. The presently-disclosed subject matter includes use of the compositions disclosed herein for the treatment of gliblastoma multiforme (GBM).

As used herein, the terms "administering" and "administration" refer to any method of providing a pharmaceutical preparation of the composition disclosed herein to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. A preparation can be administered therapeutically or prophylactically.

As used herein, the term "effective amount" refers to an amount that is sufficient to achieve the desired result or to have an effect on an undesired condition. For example, a "effective amount" refers to an amount that is sufficient to achieve the desired therapeutic result or to have an effect on undesired symptoms, but is generally insufficient to cause adverse side affects. In some embodiments, an effective amount will result in an inhibition in the growth of glioblastoma cells. In some embodiments, en effective amount will result in a killing of glioblastoma cells. In some embodiments, an effective amount will result in a reduction in undesired symptoms associated with glioblastoma. The specific therapeutically effective dose level for any particular subject will depend upon a variety of factors including the severity of the disorder; the specific composition employed; the age, body weight, general health, sex and diet of the subject; the time of administration; the route of administration; the rate of excretion of the specific compound employed; the duration of the treatment; drugs and/or radiation used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human or non human. Thus, veterinary therapeutic uses are provided in accordance with the presently disclosed subject matter. As such, the presently disclosed subject matter provides for administration to mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; rabbits, guinea pigs, and rodents. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like. The term does not denote a particular age or sex. Thus, adult and newborn subjects, as well as fetuses, whether male or female, are intended to be covered.

The term "targeting", when used herein in connection with a glioblastoma cell, refers to an ability to measurably affect the cell, e.g., decrease growth, kill, etc. In some embodiments, such measurable affect can be demonstrated relative to a control. In some embodiments, such measurable affect can be identified based on a reducing in undesired symptoms associated with glioblastoma cells in a subject. In some embodiments, such measurable affect can be identified based on a reducing in glioblastoma cells (e.g., reducing in tumor size) or in a reducing in glioblastoma cell growth (e.g., mitigation in tumor growth and/or metastasis).

As used herein, the terms "treatment" or "treating" relate to any treatment of a condition associated with a presence of a glioblastoma cell, including but not limited to prophylactic treatment and therapeutic treatment As such, the terms treatment or treating include, but are not limited to: inhibiting the progression of the condition; arresting the development of the condition; reducing the severity of the condition; ameliorating or relieving symptoms associated with the condition; and causing a regression of the condition or one or more of the symptoms associated with the condition of interest.

Compositions of the presently-disclosed subject matter include at least one FTI and at least one GSI. Examples of FTIs that can be used in accordance with the presently-disclosed subject matter include, but are not limited to, tipifarnib, lonafarnib, and L744,832. In some embodiments, the FTI is selected from tipifarnib and L744,832. In some embodiments, the FTI is tipifarnib. In some embodiments, the FTI is L744,832. Examples of GSIs that can be used in accordance with the presently-disclosed subject matter include, but are not limited to, RO4929097, MK-0752, MK-003, DAPT, compound E, MK-0752, and PF03084014. In some embodiments, the GSI is selected from RO4929097, DAPT, and compound E. In some embodiments, the GSI is RO4929097. In some embodiments, the GSI is DAPT. In some embodiments, the FTI is tipifarnib and the GSI is RO4929097. In some embodiments, the FTI is L744,832 and the GSI is DAPT.

In some embodiments, the composition including an FTI and a GSI can be provided as a radiosensitizer. In this regard, radiation can be administered in association with the administration of the composition. Examples of radiation that might be delivered and for which sensitivity is improved by making use of the claimed composition include, but are not limited to fractionated external beam radiation, 3-dimensional conformal radiation, and stereotactic radiosurgery.

In some embodiments, the composition including an FTI and a GSI can be provided as a chemosensitizer. In this regard, a chemotherapeutic agent can be administered in association with the administration of the composition. Examples of chemotherapeutic agents that might be administered and for which sensitivity is improved by making use of the claimed composition include, but are not limited to etoposide, camptothecin, and DNA-damaging agents known to those of ordinary skill in the art.

As will be recognized by one of ordinary skill in the art upon study of the present document, in some cases it could be desirable to include further ingredients in the composition as described herein. Examples of such further ingredients include, but are not limited to EGFR inhibitors, and insulin receptor/IGF-1R inhibitors.

Compositions of the presently-disclosed subject matter are useful for targeting or producing an effect against glioblastoma cells, and/or for treating glioblastoma multiforme (GBM). In some embodiments, the effect against glioblastoma cells is selected from an inhibition in the growth of glioblastoma cells, a killing of glioblastoma cells, and a reduction in symptoms associated with the presence of glioblastoma cells.

The presently disclosed subject matter further includes pharmaceutical compositions comprising the compositions including an FTI and a GSI, as disclosed herein, and a pharmaceutically-acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

As proposed herein, including an FTI and a GSI in the same composition increases the efficacy of the components of the composition, as compared their efficacy when administered separately. In some embodiments, the increase in the efficacy is more than an additive effect, and combination of the FTI and GSI can be described as having a synergistic effect.

As used herein, "synergy" and "synergistic effect" can refer to any substantial enhancement, in a composition of at least two components, of a measurable effect, when compared with the effect of a component of the composition, e.g., one active compound alone, or the complete blend of compounds minus at least one compound. Synergy is a specific feature of a composition including multiple components, and is above any background level of enhancement that would be due solely to, e.g., additive effects of any random combination of components.

Synergy is a specific feature of a composition, and is above any background level of enhancement that would be due solely to, e.g., additive effects of any random combination of ingredients. This combination has demonstrated clinically synergistic effects.

In some embodiments, a substantial enhancement of a measurable effect can be expressed as a coefficient of synergy. A coefficient of synergy is an expression of a comparison between measured effects of a composition and measured effects of a comparison composition. The comparison composition can be a component of the composition. In some embodiments, the synergy coefficient can be adjusted for differences in concentration of the complete blend and the comparison composition.

Synergy coefficients can be calculated as follows. An activity ratio (R) can be calculated by dividing the % effect of the composition (AB) by the % effect of the comparison composition (Xn), as follows:

$$R = AB/Xn. \quad\quad \text{Formula 1}$$

A concentration adjustment factor (F) can be calculated based on the concentration (Cn), i.e., % (wt/wt) or % (vol/vol), of the comparison composition in the composition, as follows:

$$F = 100/Cn \quad\quad \text{Formula 2}$$

The synergy coefficient (S) can then be calculated by multiplying the activity ratio (R) and the concentration adjustment factor (F), as follows:

$$S = (R)(F) \quad\quad \text{Formula 3}$$

As such, the synergy coefficient (S) can also by calculated, as follows:

$$S = [(AB/Xn)(100)]/Cn \quad\quad \text{Formula 4}$$

In Formula 4, AB is expressed as % effect of the blend, Xn is expressed as % effect of the comparison composition (Xn), and Cn is expressed as % (wt/wt) or % (vol/vol) concentration of the comparison composition in the blend.

In some embodiments, a coefficient of synergy of about 1.1, 1.2, 1.3, 1.4, or 1.5 can be substantial and commercially desirable. In other embodiments, the coefficient of synergy can be from about 1.6 to about 5, including but not limited to about 1.8, 2.0, 2.5, 3.0, 3.5, 4.0, and 4.5. In other embodiments, the coefficient of synergy can be from about 5 to 50, including but not limited to about 10, 15, 20, 25, 30, 35, 40, and 45. In other embodiments, the coefficient of synergy can be from about 50 to about 500, or more, including but not limited to about 50, 75, 100, 125, 150, 200, 250, 300, 350, 400, and 450. Any coefficient of synergy above 500 is also contemplated within embodiments of the compositions.

Given that a broad range of synergies can be found in various embodiments of the invention, it is expressly noted that a coefficient of synergy can be described as being "greater than" a given number and therefore not necessarily limited to being within the bounds of a range having a lower and an upper numerical limit. Likewise, in some embodiments of the invention, certain low synergy coefficients, or lower ends of ranges, are expressly excluded. Accordingly, in some embodiments, synergy can be expressed as being "greater than" a given number that constitutes a lower limit of synergy for such an embodiment. For example, in some embodiments, the synergy coefficient is equal to or greater than 25; in such an embodiment, all synergy coefficients below 25, even though substantial, are expressly excluded.

In some embodiments, synergy or synergistic effect associated with a composition can be determined using calculations similar to those described in Colby, S. R., "Calculating synergistic and antagonistic responses of herbicide combinations," Weeds (1967) 15:1, pp. 20-22, which is incorporated herein by this reference. In this regard, the following formula can be used to express an expected % effect (E) of a composition including two compounds, Compound X and Compound Y:

$$E = X + Y - (X*Y/100) \quad\quad \text{Formula 5}$$

In Formula 5, X is the measured actual % effect of Compound X in the composition, and Y is the measured actual % effect of Compound Y of the composition. The expected % effect (E) of the composition is then compared to a measured actual % effect (A) of the composition. If the actual % effect (A) that is measured differs from the expected % effect (E) as calculated by the formula, then the difference is due to an interaction of the compounds. Thus, the composition has synergy (a positive interaction of the compounds) when A>E. Further, there is a negative interaction (antagonism) when A<E.

Formula 5 can be extended to account for any number of compounds in a composition; however it becomes more complex as it is expanded, as is illustrated by the following formula for a composition including three compounds, Compound X, Compound Y, and Compound Z:

$$E = X + Y + Z - ((XY + XZ + YZ)/100) + (X*Y*Z/10000) \quad\quad \text{Formula 6}$$

In some embodiments, a composition is provided wherein the FTI and the GSI are provided in a particular ratio relative to one another. For example, in some embodiments the FTI and the GSI are provided in a ratio of about 20:1 to about 1:20, wherein the ratio is a volume ratio. In some embodiments the FTI and the GSI are provided in a ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20 (wt/wt).

Compositions as disclosed herein are useful for practicing methods of the presently-disclosed subject matter. In some embodiments, a method of the presently-disclosed subject matter includes targeting or producing an effect against a glioblastoma cell, including contacting a glioblastoma cell with a composition comprising a farnesyl transferase inhibitor (FTI) and a gamma-secretase inhibitor (GSI). In some embodiments, the effect against glioblastoma cells is selected from an inhibition in the growth of glioblastoma cells, a killing of glioblastoma cells, and a reduction in symptoms associated with the presence of glioblastoma cells.

In some embodiments, contacting a glioblastoma cell with the composition comprises administering the composition to a subject. In this regard, in some embodiments, a method includes administering an effective amount of a composition comprising a farnesyl transferase inhibitor (FTI) and a gamma-secretase inhibitor (GSI) to a subject. In some embodiments, the subject is in need of treatment for glioblastoma multiforme (GBM). In some embodiments, the method further includes administering radiation to the subject. In some embodiments, contacting a glioblastoma cell with the composition produces a synergistic effect, as compared to the effect of contacting the cell with either an FTI or a GSI, alone.

The presently-disclosed subject matter can further include a kit, which includes a composition as disclosed herein, packaged together with a second component of the kit, selected from a device for administering the composition, an additional compound or composition useful for targeting a glioblastoma cell or for treatment of GBM.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently-disclosed subject matter is further illustrated by the following specific but non-limiting examples. The following examples may include compilations of data that are representative of data gathered at various times during the course of development and experimentation related to the present invention.

EXAMPLES

Example 1

It is well established that tumor resistance to radiation is due to, at least in part, the aberrant activation of pro-survival signaling networks. Glioblastoma is well documented for its rapid recurrence following radiotherapy; however, until recently, there was a lack of mechanistic understanding for this observation. Over the last few years, it has become increasingly clear that cancer stem cells (CSCs) or tumor-propagating cells (TPCs) may represent a significant driving force underlying radiation resistance and tumor recurrence in certain human tumors, including glioblastoma (1, 2).

Glioblastoma stem cells (GSCs) appear to be more resistant to radiation than matched non-stem tumor cells (3), suggesting that they are important targets to investigate the mechanistic connections between tumor radioresistance and clinical outcomes. GSCs may acquire resistance to conventional chemoradiotherapy via activation of unique signaling networks. In this regard, the present inventor recently reported a Notch-dependent pro-survival mechanism that specifically protected GSCs from radiation-induced apoptosis. However, the signaling network underlying this novel function has yet to be fully characterized.

The present inventor's data has demonstrated that Notch-dependent activation of Akt played important roles in the radioresistant phenotype observed in GSCs. It was further demonstrated that the levels of active Ras in irradiated GSCs were significantly reduced upon Notch inhibition by γ-secretase inhibitors (GSIs). Expression of the constitutively active H-Ras V12 antagonized the radiosensitizing effects of GSIs and restored Akt activity, suggesting a Notch/Ras/Akt-mediated prosurvival mechanism in GSCs. GSI-induced inactivation of AKT could be augmented by another class of radiosensitizers, farnesyltransferase inhibitors (FTIs).

Surprisingly, administration of a combination of GSI and FTI was shown to synergistically decrease growth, neurosphere formation, and survival of GSCs. Synergistic results were also seen following radiation.

Without wishing to be bound by theory or mechanism, these effects could be due, at least in part, to interference with RhoB activity, as knockdown of RhoB abolished GSC response to FTIs while sensitized cells to GSIs. Additionally, GSCs were resistant to FTIs upon expression of the constitutively active intracellular domain of Notch2 (NICD2), suggesting crosstalk between Notch and RhoB.

Finally, FTIs and GSIs, singly or in combination, had limited impacts on survival of non-stem GBM cells. Based on these findings, the present inventor proposes that a Notch-regulated signaling network, integrating Ras and RhoB, is involved in survival of GSCs after exposure to radiation (FIG. 1).

Studies are described in these Examples, which are directed toward the following:

Notch Regulation of Survival of Irradiated GSCs Via a Ras-Mediated Signaling Network.

The present inventor's data indicate that Ras and its downstream targets were critically implicated in the Notch-dependent radioprotective mechanism. Expression of constitutive mutants of Ras (H-Ras V12) or Akt (Myr-Akt1) abolished the radiosensitizing effects of GSIs. Although mutations of these two molecules are rare in GBM, recurrent aberrations of the RTK/Ras/Akt pathway drive the malignant phenotypes in many, if not all, GBM tumors. Studies are contemplated to delineate the role of Ras and its downstream PI3K/Akt pathways in Notch-dependent radioprotective mechanism, with additional focus on upstream regulators frequently altered in GBM, such as NF-1, PTEN, EGFR and PDGFR.

GSIs and FTIs Synergistically Decrease GSC Survival and Increase Radiosensitivity.

Over the past several years, clinical trials showed that single-targeted agents generally provided only moderate benefits in a small subset of GBM patients (4). The present inventor's data indicate that GSIs and FTIs synergistically enhanced apoptosis and growth inhibition in GSCs with or without radiation. The effects of FTIs appeared to be mediated, at least in part, by targeting RhoB. Studies are contemplated to robustly assess the combinatorial effects of GSI and FTI in an orthotopic glioma mouse model and to study the combination as being more effective than single agent in a context of radiotherapy with overall survival as the primary endpoint.

GBM-Associated Genomic Aberrations May Predict Tumor Response to Notch-Targeted Combination Therapy.

GBM is highly heterogeneous at molecular levels and vary in response to targeted therapies. More than 35 GBM xenografts have been collected and samples with drastically different sensitivities to GSI, FTI, and/or radiation have been identified. Thus, studies are contemplated to characterize these samples at molecular levels, with focus on the molecules implicated in the Notch-dependent radioprotective signaling network and correlate with tumor response to identify potential molecular biomarkers. These markers will be subsequently validated by genetic targeting approaches and interrogated in human specimens.

Overview:

Glioblastoma is a highly lethal disease due to, at least in part, its resistance to conventional chemoradiotherapy. More effective molecularly targeted therapies hold the promise to improve clinical outcomes of GBM. However, results from recent clinical trials have shown that single-targeted agents at best provided modest benefits to a small subset of GBM patients (5). Two fundamental challenges need to be addressed to improve targeted treatment for GBM. First, GBM tumors are driven by aberrant signaling networks instead of individual driver mutations; thus simultaneous targeting at multiple central nodes (hubs) of the signaling networks may be proven to be more effective than single-agent therapy. Notably, the cancer stem cell fraction of GBM may be sustained by signaling networks different from the bulk tumor cells (6). Second, GBM tumors are highly heterogeneous at molecular levels. Therefore, patients should be selectively treated according to the molecular profiles of their tumors. The studies are centralized on rational design of novel combination therapies that may substantially improve the efficacy of radiotherapy for GBM through targeting the CSC subpopulation as well as explore molecular markers that may predict tumor response.

Targeting GBM Stem Cells:

It has been well documented that tumors comprise heterogeneous populations of neoplastic cells as well as non-neoplastic cells (7). Whether all neoplastic cells within a tumor are functionally equal is an important question in research as well in clinics (8). The emerging cancer stem cell hypothesis suggests a hierarchical organization of tumors in which a subpopulation of tumor cells with stem cell-like phenotypes drives tumor progression (9). These cells are termed cancer stem cells (CSCs) for their ability of self-renewal and generation of differentiated progenies. Alternatively, they are called tumor-initiating cells (TICs) or tumor-propagating cells (TGCs) for their ability to recapitulate the original tumors in serial xenotransplantation assays. While not all tumor may fit the cancer stem cell model, there has been accumulating evidence that primary brain tumors, such as medulloblastoma or glioblastoma, are organized in a hierarchical manner (10-12). The work and studies from other laboratories demonstrate that the CSC subpopulations in these tumors can be prospectively enriched by selection for cell surface markers, such as CD133, CD15/SSEA-1, L1CAM, and more recently, integrin α6 (11-15). Expression of CSC markers, particularly CD133, has been linked to poor prognosis (16, 17).

Two key observations highlight the significance of targeting GSCs or compromising their resistance to chemoradiotherapy. First, GSCs are highly tumorigenic. Hundreds of GSCs are usually sufficient to generate xenograft tumors in serial transplantation assays, whereas differentiated cancer cells fail to do so at numbers several orders of magnitude higher (3, 11, 12, 15, 18). Second, GSCs are more resistant to chemoradiotherapy than their differentiated progenies (19). GBM tumors often well respond to radiotherapy in the first place, but rapid tumor recurrence inevitably lead to patient death (20). This observation can be explained by the abilities of GSCs to survive radiation and to efficient repopulate tumors. Additionally, the reduced sensitivity of recurrent tumors toward radiation may be due to, at least in part, the expansion of GSCs following radiation exposure (3). It is also reported that GSCs are less sensitive to chemotherapeutic agents, including temozolomide, which is used as standard treatment for GBM (21-24). Additionally, clinical data showed that the percentage of CSC-like subpopulation in breast cancer specimens increased following administration of chemo drugs but not lapatinib, a dual inhibitor of EGFR and HER2 (25). Therefore, it is proposed to develop more effective treatments for GBM through targeting the pro-survival mechanisms in the GSC subpopulation.

Figure 2:
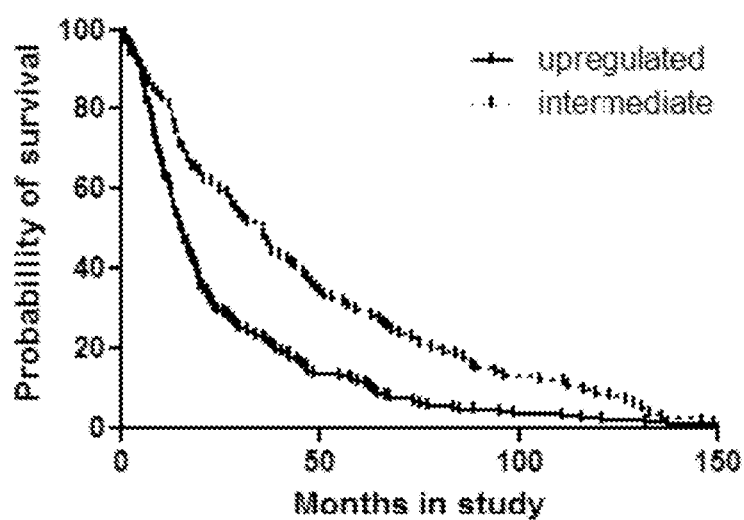
FIG. 2 shows that expression of Jag1, a Notch ligand, correlates with poor prognosis of glioma patient. Clinic data from REMBRANDT suggest that high Jag1 expression correlates with poor survival. p=3.7E-9, upregulated (229) vs. Intermediate (114).

Notch as a Therapeutic Target in GBM:

The concept of targeting the Notch signaling pathway as a therapeutic strategy for cancer treatment has received increasing interest (26, 27). The Notch signaling pathway is orchestrated by four receptors (Notch1-4) and five membrane-bound ligands (Jag1, Jag2, Dll1, Dll3 and Dll4). Ligand binding induces multiple steps of proteolytic cleavage of the membrane-bound Notch receptors, leading to release and nuclear translocation of the intracellular domains of Notch receptors, which subsequently activates Notch-dependent transcription (28). Notch signaling has pleiotropic roles in embryonic development and homeostasis of adult tissues through directing cell-fate determination of stem cell and progenitors (29). Aberrant Notch activation has been documented in a wide range of human cancers, such as breast cancer (30), T-cell acute lymphoblastic leukemia (T-ALL) (31), as well as GBM (32, 33). REMBRANDT (Repository for Molecular Brain Neoplasia Data, https://caintegrator.nci.nih.gov/rembrandt/) data suggest that high expression levels of several Notch pathway elements, such as Jag1, Dll4 or Notch3, correlate with poor prognosis in glioma (FIG. 2 and data not shown). Notch activity regulates tumor cell proliferation and survival through crosstalk with core oncogenic pathways, such as EGFR, RAS, and PI3K/AKT (26). Of particular interest, several recent studies including the work demonstrated that pharmaceutical or genetic inhibition of Notch impaired GSC survival and tumorigenicity and rendered these cells more sensitive to radiation and chemotherapeutic agents (34-38). On the basis of these findings, the study was to delineate underlying molecular mechanisms and design more effective combination treatment.

Therapeutic Potential of Farnesyltransferase Inhibitors (FTIs):

FTIs have been extensively studied for their anticancer and radiosensitizing effects in laboratories as well as in clinic trials (39). These drugs were originally developed to interfere with Ras signaling, as Ras activation requires farnesylation. However, subsequent studies showed that K-Ras and N-Ras evade the function of FTIs via a closely related alternative modification, geranylgeranylation. Alternative targets have been identified to interpret the functions of FTIs. RhoB is a small GTPase that regulates cytoskeleton dynamics, cell migration and growth. It has been shown to be a critical FTI target and mediate DNA damage-induced apoptosis (40-43). Additionally, FTIs may induce apoptosis by inhibiting PI3K/Akt pathway through an unidentified farnesylated protein (44). Although their targets remain elusive, FTIs demonstrate potent anticancer activities in preclinical models, well tolerated in phase I trials, thus leading to a number of clinical trials in various human cancers including GBM (39). The most promising effects were observed in acute myeloid leukemia (45, 46). However, FTIs as single-agent therapy show at best moderate effects in a small percentage (~10%) of GBM patients even in combination with radiotherapy (47-50). Thus, much remains to be learned to optimize FTI-based therapy by combining with other treatments and determining the factors that predict response.

Molecular Diversity of GBM:

GBM tumors are highly heterogeneous in the molecular basis of their pathology. It is not surprising that newly developed therapies that selectively inhibit one or even multiple molecular targets are only effective in a small subset of patients (51, 52). Multiple molecularly distinguished GBM subtypes have been identified on the basis of global gene expression profiles and showed better correlation with survival than traditional histological classification (53-57). For example, the Cancer Genome Atlas (TCGA) network defined four molecular GBM subtypes, namely proneural, classical, mesenchymal and neural subtypes (57). Comprehensive genomic analyses also identified novel tumor suppressors in GBM, such as IDH1 and NF1, and generated new insights into the core GBM signaling pathways (55, 58). Collectively, these studies indicate that the RTK/Ras/PI3K/Akt signaling network appears to be the most frequently activated oncogenic mechanism in GBM. Interestingly, this signaling network may be activated via distinct mechanisms in different molecular subtypes. The proneural subtype is enriched for high PDGFR expression and mutations; the classic subtype is distinguished by high level amplification and mutations of EGFR, while the mesenchymal subtype includes most mutations and deletions of NF-1, which encodes a Ras inhibitor (57). Similarly, an proteomics-based study also identified GBM subtypes that were each associated with activation of EGFR, PDGFR, or RAS (59), suggesting that alterations of these molecules may define distinct growth and survival mechanisms in GBM. The components of Notch pathway are also differentially expressed in molecular GBM subtypes, with Notch3 and Jag-1 highly expressed in the classical subtype and Dll3 upregulated in the proneural subtype (54, 57, 59), suggesting Notch-dependence may vary among molecularly distinguished GBM. Preclinical models that resemble the molecular heterogeneity of human GBM have not been adequately developed. It has been shown that GBM xenografts but not established cell lines resemble patient tumors in expression profiles. A xenograft tumor panel will be used to model the complexity of human disease for novel therapeutics development and biomarker discovery.

Overview: Making GBM More Sensitive to Radiotherapy by Novel Approaches that Effectively Target the Radioresistant Cancer Stem Cell Subpopulation Radiotherapy is the most effective non-surgical intervention for GBM and the first-line treatment for inoperable tumors. The CSC subpopulation of GBM has emerged as a key target for radiotherapy due to its strong tumorigenicity and resistance to radiation and other genotoxic stresses. To improve the efficacy of radiotherapy for GBM, exploration of novel molecular mechanisms that support GSC survival following exposure to radiation has been initiated. The present inventor's recent study identified a Notch-dependent prosurvival signaling network that specifically protected GBM stem cells from radiation-induced apoptotic death. Notch signaling was upregulated in GSCs following radiation. Blockage of Notch signaling by pharmaceutic or genetic approaches significantly increased apoptosis and decreased clonogenic survival in irradiated GSCs, suggesting that Notch-targeted agents held great promise to improve radiotherapy for GBM treatment. Multiple clinical trials using GSIs to treat GBM and other solid tumors have been initiated after the previous study published in early 2010, including ones that combined GSI with radiation and/or chemotherapeutic drugs (www-.clinicaltrials.gov, NCT01119599 etc.). However, much remains to be learned to optimize this novel therapeutic paradigm. Thus, studies were extended toward a better mechanistic understanding, a more effective combination treatment, and a preclinical model that facilitates discovery of biomarkers and design of patient-tailored clinical trials. Results reviewed below are anticipated to lay the foundation for a novel paradigm of GBM treatment that targets the Notch-dependent pro-survival signaling network in GSCs.

Notch Promotes GSC Survival Following Exposure to Ionizing Radiation

Figure 3:
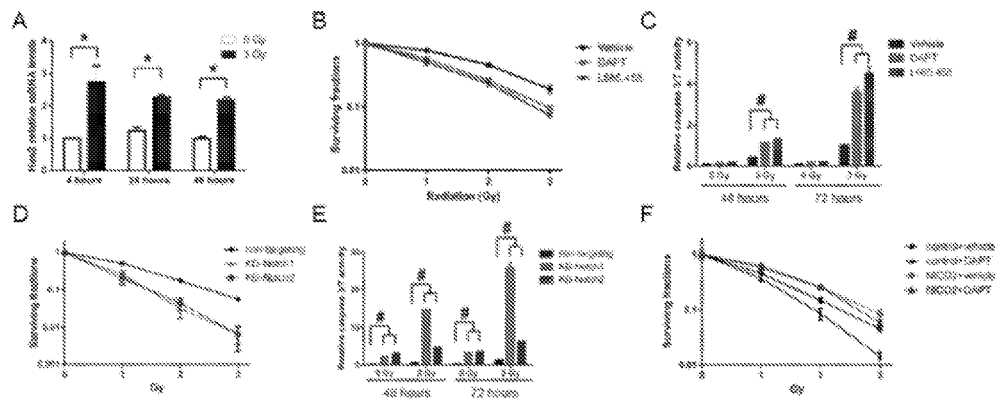
FIG. 3 shows that Notch promotes GSC survival following radiation. (A) T4302 CD133+ GBM stem cells were enriched from freshly collected subcutaneous xenograft tumors, cultured in stem cell media. Cells were left unirradiated or irradiated at 3 Gy. The relative mRNA levels of Hes2 were determined by quantitative real-time PCR at the time points as indicated. (B) T4302 CD133+ cells were pre-treated with vehicle (DMSO), 2 µM DAPT or 0.5 µM L685,458 for 4 hours and irradiated as indicated. Cells were then plated to form neurospheres. Fourteen days after plating, neurospheres containing more than 50 cells were scored. To determine the surviving fractions, the number of neurosphere at each radiation dose was normalized to that of the corresponding sham-irradiated group. (C) T4302 CD133+ cells were treated with GSIs±radiation as indicated. Relative caspase 3/7 activities were determined by normalizing caspase activities to the corresponding cell numbers. (D), (E) T4302 CD133+ cells were infected with lentivirus directing expression of non-targeting shRNA or shRNAs specific to Notch1 or Notch2 (KD-Notch1 or KD-Notch2), and selected with puromycin. Relative caspase 3/7 activities and clonogenic survival were determined as described above. (F) T4302 CD133+ cells were infected with control lentivirus or lentivirus directing expression of NICD2. Clonogenic survival was determined as described above. *: $p<0.05$ by Student's t-test; #: $p<0.01$ by one-way ANOVA.

In previously published study, the present inventor demonstrated that Notch activity was required for GSC survival following exposure to ionizing radiation. Using CD133+ cells enriched from GBM xenograft tumors, it was demonstrated that radiation induced transcriptional activation of multiple Notch target genes, including Hes2 and Hes5, as well as a Notch-responsive luciferase reporter (FIG. 3A and data not shown). Blockage of Notch signaling by γ-secretase inhibitors, DAPT or L-685,458, increased apoptotic cell death and reduced clonogenic survival in GSCs following 3-Gy X-ray radiation (FIGS. 3B and 3C). Conversely, in the absence of radiation, GSIs showed moderate cytostatic effects and did not induce significant apoptosis (FIG. 3C and data not shown). Knockdown of Notch1 or Notch2 sensitized GSCs to radiation in a similar manner as GSIs, suggesting that Notch signaling is the primary target of GSIs (FIGS. 3D and 3E). Additionally, expression of the constitutively active intracellular domain of Notch2 (NICD2), which was not sensitive to GSIs, made GSCs resistant to radiation as well as GSIs (FIG. 3F), suggesting that tumor microenvironmental cues, such as hypoxia or perivascular niche, may protect GSCs from radiation by activating Notch. Interestingly, targeting Notch, either by GSIs or knockdown of Notch, had limited effects on survival of CD133− non-stem GBM cells irrespective of radiation (data not shown), suggesting there are substantial differences in response to radiation in GSCs relative to non-stem GBM cells. Taken together, these data demonstrate that a novel Notch-dependent mechanism is essential for cellular survival in GSCs following ionizing radiation.

Notch Regulates GSC Post-Radiation Growth and Survival in a Ras-Dependent Manner Notch regulates tumor cell proliferation and survival through crosstalk with several key oncogenic signaling pathways, such as EGFR, Ras and PI3K/Akt (28, 60, 61). Aberrant activation of these pathways in GBM has been well documented (57). It is therefore important to interrogate the mechanistic connections between Notch and these pathways in regulation of GSC biology and to determine if these connections affect tumor response to Notch-targeted agents. It has been previously reported that Akt activity was required for GSC survival (62). It was therefore determined whether Akt activity was implicated in the Notch-dependent radioresistant mechanism. The results showed that apoptosis induced by Notch blockage in irradiated GSCs was associated with reduced Akt activity as shown by decreased phosphorylation at S473 (FIG. 4A, lane 6 vs. lane 5). Notch activation by expression of NICD2 enhanced radiation-induced Akt activation in the absence as well as presence of DAPT treatment (FIG. 4A). Finally, NICD2 expression failed to rescue GSCs from apoptosis induced by chemical inhibition of PI3K or Akt (FIG. 4B). These results collectively suggest that the Notch-dependent pro-survival mechanism is mediated, at least in part, by activation of the PI3K/Akt pathway.

Potential mechanisms that mediate Notch-dependent Akt activation were examined next. Previous work did not support a number of previously reported mechanisms, such as down-regulation of PTEN and activation of p56Lck (34, 61, 63). The present inventor then interrogated the interaction between Notch and Ras, a direct activator of PI3k/Akt. Using an active Ras pull-down assay kit (Pierce), the activation status of Ras signaling can be determined as the amount of Ras-GTP co-purified with a GST-tagged Ras-binding domain of c-Raf. Notch inhibition by GSI-treatment did not alter total Ras protein levels but decreased active Ras levels after radiation exposure (FIG. 4C). Additionally, lentivirus-mediated expression of H-Ras V12, a constitutively active Ras mutant, abolished the ability of GSIs to inhibit growth, increase apoptosis, and downregulate Akt activity in GSCs (FIG. 4D-4F). These data collectively suggest that Notch regulates GSC growth and survival through a Ras/Akt mediated signaling network. Another Ras downstream pathway, the Raf/MEK/ERK MAPK cascade, was also downregulated upon GSI-treatment (data not shown). However, targeting this pathway by two different MEK inhibitors did not significantly alter GSC growth and survival, and showed at best additive interaction with GSIs (data not shown). Additionally, aberration of this MAPK pathway is rare in GBM, although mutations of BRAF are implicated in a subset of low-grade gliomas (64, 65). Therefore, the study proposed in this application will focus on the PI3K/Akt as the main pathway downstream of Ras. It has been well established that Ras (H-Ras, K-Ras, N-Ras) represents one of the most frequently altered oncogene families and a therapeutic target of paramount significance in human tumors. Unlike many other solid tumors, Ras mutations are rare in GBM. However, a large body of aberrations found in GBM, either activate Ras, such as alterations of NF1, EGFR and PDGFR; or activate Ras downstream signals, such as PI3K/Akt. Therefore, the finding that Notch inhibition by GSIs reduces Ras activity following radiation has important clinical significance and warrants further investigation.

Combination of GSI and FTI Synergistically Targets GSCs

Figure 5:
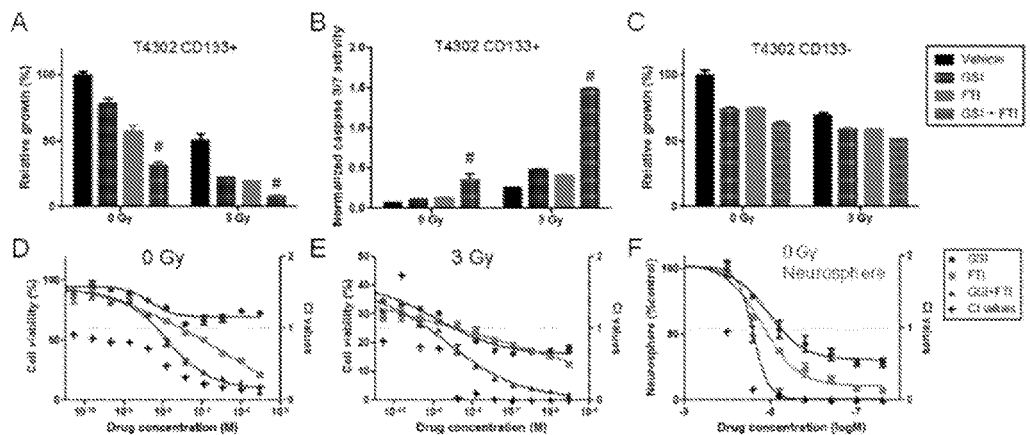
FIG. 5 shows that GSI and FTI synergistically decrease growth and survival of GSCs. (A, B) T4302 CD133+ cells were treated with 100 nM RO4929097 (GSI) and/or 100 nM tipifarnib (FTI) for 4 hours prior to 3 Gy radiation. (A) Cell growth on day 5 and (B) caspase 3/7 activation on day 3 were determined as described in FIG. 4. #: $p<0.001$ by one-way ANOVA, combo vs. single agents. (C) The effects of GSIs and FTI against growth of T4302 CD133− cells were determined as described in panel A. (D, E) T4302 CD133+ cells were treated with GSI, FTI, or a 1:1 mixture at different concentrations (ranging from 3000 nM to ~0.5 nM, 1:3 dilution)±3 Gy radiation. Cell viability was determined at 5 days after treatment in comparison to vehicle-treated groups. The right-hand Y axis shows the CI value calculated by the Chou-Talalay method (Compusyn software). (F) T4302 CD 133+ cells were treated by GSI±FTI with a 2-fold dilution. Neurospheres were countered on day 10, and normalized to the vehicle-treated group.

The present inventor has started to explore if agents targeting the Ras signaling may augment the radiosensitizing effects of GSIs. As discussed above, farnesyltransferase inhibitors (FTIs) were selected for their favorable pharmacological features, well-documented radiosensitizing activities, and ability to target H-Ras. The present inventor assessed the effects of the combination of GSI and FTI on growth and survival of GSCs±radiation. The degree of growth inhibition after 5-day treatment observed with the combination of GSI and FTI was significantly higher than either agent alone irrespective of radiation (FIG. 5A). In the absence of radiation, the combination of GSI and FTI induced significant caspase activation but not GSI or FTI alone (FIG. 5B). Following 3-Gy radiation, GSI or FTI alone increased caspase 3/7 activity approximately 2 fold compared with the sham-treated group, whereas the combination increased caspase activity for more than 5 folds. In contrast, the combination of GSI and FTI had limited impact on growth of CD133− glioblastoma cells (FIG. 5C). As the combination of GSI and FTI demonstrated potentially greater-than-additive effects, the present inventor assessed if these two compounds have synergistic effects on the growth and neurosphere formation in GSCs using the Chou-Talalay method (66). Except a few data points for concentration <5 nM, the combination index values of GSI and FTI on growth inhibition of GSCs were substantially lower than 1, indicating synergistic effects (FIGS. 5D and 5E). Importantly, the synergy was not dependent on radiation. Similarly, the combination synergistically inhibited neurosphere formation of GSCs without radiation (FIG. 5 F, CI<1 for all data points). We next assessed the impact of the GSI and FTI combination on Ras/Akt activity in GSCs (FIG. 7B). Surprisingly, FTIs did not enhance GSI-induced Ras inhibition (FIG. 7B). In contrast, the combination of GSI and FTI decreased phosphorylation of Akt at not only serine 473 but also threonine 308 to much lower levels compared with single agent (FIG. 7B), suggesting that the synergistic interaction of this combination may be, at least in part, mediated by a greater Akt inhibition. These results also suggest that Akt is regulated by both Ras-dependent and Ras-independent mechanisms. Additionally, Notch activation by NICD2 expression significantly attenuated the ability of FTIs to inhibit growth and induce apoptosis in GSCs, particularly after radiation (FIGS. 9A and 9B). Taken together, the data suggest that GSIs and FTIs synergistically target a critical growth and survival signaling network in GSCs and that Notch functions as a central hub of this signaling network.

RhoB is the Primary Target of FTI in GSCs

Figure 6:
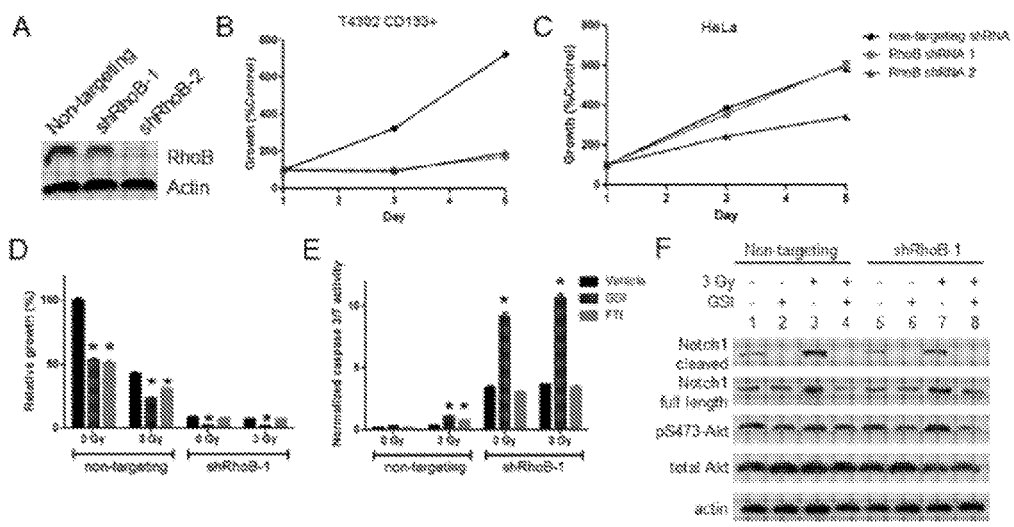
FIG. 6 shows that RhoB mediates FTI activities in GSCs. (A) T4302 CD133+ cells were infected with lentivirus directing expression of a non-targeting shRNA or two RhoB specific shRNA. Cells were lysed for immunoblotting 3 days after infection. (B, C) Two days after infection, cells were selected with puromycin for two days, and plated in 96-well plates for growth curve assays. Cell growth was measured on days 1, 3 and 5 after plating, and normalized to the corresponding readout on day 1. (D-F) After lentiviral infection and puromycin selection as described above, T4302 CD133+ cells were treated with 100 nM GSI, FTI, ±3 Gy radiation and plated for subsequent experiments. (D) Relative growth on day 5, (E) caspase activation on day 3, and (F) protein levels on day 1 after treatment were determined as described in FIG. 4. *: $p<0.001$ by Student's t-test in comparison to the corresponding control groups.

FTI did not alter active Ras levels (FIG. 7B), suggesting that H-Ras may have minor contribution to total Ras activity in GSCs. It has been reported that targeting RhoB is required for FTI to enhance apoptosis after ionizing radiation (42, 67). The present inventor next determined if RhoB was a key target of FTIs in GSCs. RhoB expression was downregulated by two previously reported lentivirus that encoded RhoB specific shRNA (Open Biosystem, TRCN0000047851 and 47852) (FIG. 6A) (67). Knockdown of RhoB drastically reduced growth and increased cell death in T4302 CD133+ cells and several additional lines (FIG. 6B and data not shown). In contrast, RhoB was essentially dispensable for HeLa cells, suggesting tissue-specific roles of RhoB (FIG. 6C). In addition, the half maximal inhibitory concentrations ($IC_{50}$) of FTI (tipifarnib) in HeLa were in the low µM range, at least one magnitude higher than those found in GSCs (data not shown). Cells expressing RhoB shRNA demonstrated impaired growth and increased apoptosis (FIGS. 6D and 6E). Interestingly, these cells were insensitive to FTI but highly sensitive to GSIs, suggesting that loss of RhoB mimic the function of FTIs (FIGS. 6D and 6E). Additionally, GSI treatment induced a greater reduction of Akt phosphorylation in RhoB knockdown cells compared with control cells (FIG. 6F). Taken together, these data suggest that RhoB may play an important role in GSCs and can be targeted by FTIs. The potential role of RhoB and the impact of its farnesylation will be further examined by experiments proposed herein.

Response to GSIs and FTIs Varies Significantly Among GBM Tumors

It has been repeatedly found that, with a few exceptions, targeted-therapies only generate response in a small percentage of patients, largely due to the genomic heterogeneity of their tumors (68). The present inventor showed the marked efficacies of GSIs and/or FTIs in CD133+ GSCs enriched from several GBM tumors and wanted to examine the sensitivity to GSI/FTI in a broader spectrum of GBM tumors. Work is now extended to a set of subcutaneous GBM xenografts (GBM) established by Dr. Jann Sarkaria and colleagues at Mayo Clinic. These samples are known to have mutational status of EGFR, p53 and PTEN and different radiosensitivity (FIG. 8A) (69-71). Because the cancer stem cell identity of CD133+ of the Mayo Clinic samples has not been validated by functional assays, the present inventor used the neurosphere culture that is widely utilized as a surrogate of GSCs for its ability to enrich GSC-like population (72, 73). Tumor response to GSI, FTI and/or radiation was determined as growth inhibition on day 5 after treatment, with a greater than 30% cell number reduction was defined as positive response mimicking the RECIST criteria (FIG. 8B). GBM 44 did not respond to radiation (14% growth inhibition) and marginally responded to FTI (23.4±6.4% inhibition at 0 Gy and 42±7.2% inhibition at 3 Gy), but sensitive to GSI (48±3.2% at 0 Gy and 65±3.3% at 3 Gy). The combination of radiation, GSI and FTI generated the most effective growth inhibition (85% growth inhibition vs. the untreated group). In GBM6, only the combination of radiation, GSI and FTI resulted in a significant growth inhibition (36±5.2% vs. untreated). GBM43 showed moderate response to GSI and/or FTI, but the effects of these compounds diminished after radiation. In contrast, GBM 22 did not apparently respond to any of these treatments even in combination. Taken together, the preliminary results have validated the feasibility of the methodology and demonstrated the significant variability to the combination treatment among GBM tumors. Therefore, the present inventor will continuously expand the GBM panel and determine the genomic features of all samples with focus on prevalent GBM-associated aberrations. On the basis of this molecularly characterized tumor panel, the present inventor will start to explore the potential biomarkers that may predict tumor response to the combination therapy of radiation, GSI and FTI by experiments described in herein.

Approach

Overview:

As described above, the preliminary studies have generated several lines of key observations: 1) Notch regulates GSC survival, at least in part, via the Ras/PI3K/Akt pathway in a radiation-dependent manner; 2) GSI and FTI synergistically decrease GSC survival by targeting Notch and RhoB, respectively; 3) spheroid cultures derived from subcutaneous GBM xenografts significantly differ in response to single agents or the combination. The studies proposed in this application are built upon these novel observations and have two related objectives. First, the present inventor proposes to develop a novel GSI+FTI combination that improves the efficacy of radiotherapy for GBM treatment. Second, using a GBM xenografts panel, the present inventor will start to explore predictive biomarkers for this combination therapy, with a focus on mutations and other aberrations altering molecules that are implicated in this signaling network, such as Notch ligands/receptors, EGFR, PDGFR, NF-1, PTEN and PI3K. To achieve these objectives, experiments are proposed in three specific aims. These experiments will be performed in parallel as they are not dependent on the successful completion of the other aims.

Determine Whether Notch Regulates Survival of Irradiated GSCs Via a Ras-Mediated Signaling Network.

Rationale:

It has been reported that Notch activity may promote tumor cell proliferation and survival through crosstalk with other oncogenic proteins, such as EGFR, Ras, and PI3K/Akt (26). Interestingly, these molecules are among the most frequently altered targets in GBM. While both cooperation and antagonism between Notch and Ras have been described during embryogenesis, cooperation between these two molecules appears to be important for tumor initiation (60). Notch activity is required for Ras-mediated transformation of human fibroblasts (74). On the other hand, mammary tumors induced by an oncogenic Notch4 mutant required activation of Ras and downstream signals, such as Raf/MEK/ERK and PI3K/Akt (75, 76). Ras signaling is activated by aberrations frequently found in GBM, such as activation of receptor tyrosine kinases or NF-1 inactivation (57), and promotes the neoplastic phenotype as well as radioresistance of GBM (77, 78). However, little is known about how Ras is regulated following radiation exposure. The preliminary studies showed that GSIs reduced levels of active Ras in a radiation-dependent manner and that deregulated Ras mutant compromised the effects of GSIs, suggesting that, after radiation exposure, Ras is specifically regulated by a Notch-mediated mechanism. The present inventor therefore will interrogate the biological roles and mechanisms of the functional interaction between Notch and Ras in GSC survival following radiation.

Determine the Role of Ras in Notch-Mediated Radioprotective Mechanism.

The preliminary studies demonstrated that levels of active Ras were decreased by GSI-treatment in the presence of ionizing radiation. As the targets of GSIs are not limited to Notch signaling, the hypothesis will be validated by more specific genetic targeting approaches. The present inventor will first determine if Ras is activated by ectopic expression of the active mutants NICD1, NICD2 or Notch ligand, Jag-1. The present inventor has previously shown that knockdown of Notch1 or Notch2 rendered GSCs more sensitive to radiation (34). The role of individual Notch receptors or ligands in Ras regulation will be determined by the same strategy. Additionally, the present inventor proposes to establish the interaction between Notch and individual Ras isoforms. The Ras pull down assay in preliminary study utilized a pan-Ras antibody to detect active Ras proteins bound to purified c-Raf-protein binding domain. The results will be validated by antibodies specific to individual Ras proteins to determine if Notch differentially regulates Ras isoforms. Because the c-Raf protein binding domain may selectively bind to different Ras isoforms, the present inventor will knockdown individual Ras proteins to determine the biological role of Ras in GSCs as well as their function in Notch-regulated signaling network. In mammalian, both the Notch and Ras signaling are sustained by multiple functionally overlapping but distinguished protein isoforms. There experiments will validate the hypothesis and further delineate the functions of individual isoforms with a goal to highlight the most important target within this signaling network. This is particularly important for the Notch pathway, as it can be targeted by neutralizing antibodies specific to individual receptors or ligands (79).

Determine the Mechanisms by which Notch Regulates Ras with a Focus on EGFR, PDGFR, and NF-1.

Ras mutations are rare in GBM, however, it is frequently activated by a variety of mechanisms, such as gain-of-function of receptor tyrosine kinases, particularly EGFR and PDGFR; or loss-of-function of NF-1, a GTPase activating protein of Ras (57). Notch may regulate Ras activity through altering these molecules. The crosstalk between EGFR and Notch can be activating or antagonistic. Notch may activate EGFR transcription in a p53-dependent manner in gliomas (80). Concurrent targeting of Notch and EGFR induces synthetic lethality in basal-like breast cancer (81). In contrast, it is recently reported that reciprocal inhibition between EGFR and Notch plays a critical role in cell fate determination of neural stem cells and neural progenitor cells (82). On the other hand, regulation of PDGFR and NF-1 by Notch remains largely unclear, although upregulation of PDGFRA expression by Notch has been reported (83). The present inventor has started to explore these interactions and showed that Notch inhibition by GSIs or Notch activation by NICD2 expression did not significantly alter mRNA levels of either EGFR or PDGFRA as measured by quantitative real-time PCR (data not shown). The present inventor will next determine if Notch alters protein levels and post-translational modifications of EGFR or its interaction with downstream molecules that activates Ras and Akt, such as Grb2 and PIK3R. It will also be assessed if Notch and EGFR directly bind. If data suggest that Notch alters EGFR activity, the present inventor will determine whether EGFRvIII or other active EGFR mutants, particularly these frequently found in GBM, alter the regulation of Ras by Notch. The functional interaction between PDGFR and Notch will be interrogated by a similar strategy. Crosstalk between NF-1 and Notch has not been described. The present inventor will determine if Notch alters mRNA and protein levels of NF-1 and if knockdown of NF-1 or introducing NF-1 dominant negative mutants abolishes the regulation of Ras by Notch.

Compare the Differential Role of Notch/Ras Interaction in GSCs Vs. Non-Stem GBM Cells.

The previous study has demonstrated that genetic or pharmacological targeting of Notch did not alter survival as well as Akt activity in non-stem GBM cells (34). There are two hypotheses: first, Notch does not regulate Ras in non-stem GBM cells; second, Ras is regulated by Notch signaling, but Ras activity is dispensable for non-stem GBM cells or does not regulate Akt. The present inventor will examine these two hypotheses with a goal to better understand the role of the Notch/Ras/Akt signaling pathway in GBM.

Methods. Methods of the experiments proposed in this aim are either standard or have been described in details in the recent publications (14, 34, 84, 85).

Enrichment and Culture of GBM Stem Cells:

Tumor cells are enzymatically dissociated from freshly collected GBM xenograft tumors and cultured overnight before sorting. The CD133− and CD133+ fractions are separated either by magnetic sorting using the CD133 Microbead kit (Miltenyi Biotech), or labeled with APC-conjugated CD133 antibody (Miltenyi Biotech) and sorted by flow cytometry. CD133+ cells are maintained in neurobasal media supplemented with 2% B-27, 20 ng/ml EGF and bFGF. CD133− cells are maintained in DMEM supplemented with 10% FBS but are changed into stem cell media at least 24 hours prior to experiments to control differences in cell media.

Statistical Analysis:

The p value will be calculated by ANOVA comparison or student's t-test using the GraphPad Prism software. The p-values less than 0.05 are considered significant. All data points will be repeated at least in triplicate for each experiment.

Expected Results and Analysis:

Completion of the experiments outlined in this aim is anticipated to delineate the mechanistic link between Notch and the RTK/Ras/PI3K/Akt signaling network, which is deregulated in most, if not all, GBM tumors. As Notch can be activated by ligand expressed on neighboring cells or other tumor microenvironmental cues, such as hypoxia, perivascular niche, and nitric oxide (86-89), the studies could therefore provide important insights into a novel mechanism through which microenvironment regulates tumor response to treatment. It will also be assessed if GBM-associated aberrations of this signaling network, such as EGFR mutations, NF-1 loss, or PTEN loss, will alter tumor dependence of Notch activity. Collectively, these results are expected to provide directions for rational design of novel combination therapy and patient stratification. Finally, these findings may validate results generated by experiments proposed in specific aim 3 using a GBM test panel, which harbors aberrations of the RTK/Ras/PI3K/Akt signaling network.

Potential Alternatives:

As one of central hubs of tumor signaling for proliferation and survival, Ras can be regulated by a wide variety of mechanisms. In addition to EGFR and PDGFR, Met is another receptor tyrosine kinase that can activate Ras and is also frequently amplified in GBM (57). Little is known about the interaction between Notch and Met. If Notch does not regulate other related RTK, such as EGFR and PDGFR, the present inventor will interrogate this functional interaction. Additionally, the interaction between Notch and FGFR will be assessed as bFGF (20 ng/ml) is presented in stem cell media to maintain the self-renewal and survival of GSCs in culture. Although not the focus of the study proposed in this application, the present inventor will also determine if the pro-survival and radioprotective functions of Notch is dependent on its transcriptional activation activity, using a transcriptional activation domain deficient form of NICD2. If the results are positive, the present inventor will explore the impact of GSI-treatment as well as NICD2 expression on expression profiles of GSCs using techniques such as microarray or RNA-seq. These studies may provide insights into the activities of Notch in addition to regulation the RTK/Ras/Akt pathway.

Determine Whether GSIs and FTIs Synergistically Decrease GSC Survival and Increase Radiosensitivity.

Rationale:

There is general agreement that the redundancy and compensation of the deregulated signaling network makes tumors resistant to treatment (8). Targeting single molecules within a complex signaling network often results in limited efficacy. One strategy to overcome this challenge is to develop more effective combination therapies that synergistically target the signaling network through inhibiting multiple signaling hubs. Farnesyltransferase inhibitors (FTIs) have been extensively studied for their anti-cancer efficacy and radiosensitizing potential (39). These agents show potent anti-cancer activities in preclinical settings but only modest to little efficacy in clinical trials (39). The preliminary study demonstrated that FTI augmented the ability of GSI to inhibit growth and survival of GSCs (FIGS. 5A and 5B). Importantly, the interaction between GSI and FTI appeared to be synergistic (FIGS. 5D and 5E). In GSCs exposed to 3-Gy radiation, concurrent administration of GSI and FTI could increase the growth inhibition rate from less than 50% to approximately 90% (FIG. 5, 8, 9 and data not shown), warranting further investigation of its anti-GBM potential. Additionally, the data suggest that the primary target of FTI in GSCs is RhoB (FIG. 6), thus the synergistic interaction between GSIs and FTIs is not dependent on non-specific targeting. Based on these preliminary results, the present inventor reasoned that a combination therapy including GSI, FTI and radiation might result in more effective control of GBM. Therefore, experiments are proposed to interrogate the efficacy and mechanisms of this combination in vitro as well as in vivo.

Determine the Synergistic Interaction Between GSIs and FTIs.

The preliminary results showed that combination of RO4929097 (GSI) and Tipifarnib (FTI) resulted in greater inhibition of cell growth, neurosphere formation and apoptosis than single agent treatment in CD133+ GBM cells irrespective of radiation. According to calculations based on the Chou-Talalay method (66), the combination index (CI) values of the combinatorial effects of GSI and FTI were less than 1 for all data points at concentration >5 nM, indicating drug synergy. This synergy will be validated by additional GSC samples as well as other chemically unrelated compounds, such as DAPT (GSI) and Lonafarnib (FTI), using growth inhibition at day 5 and neurosphere formation as the primary endpoint.

Determine the Role of RhoB in Growth and Survival of GSCs.

The exact mechanism of action of FTI remains unclear. RhoB exists as both farnesylated (RhoB-F) and geranylgeranylated (RhoB-GG) forms in cells, thus is a FTI target. While genetic mouse models are suggestive of a tumor suppressor role of RhoB (90), in human cells, RhoB activity is required for Ras-dependent transformation (91) as well as DNA damage-induced apoptosis (42). Additionally, the anti-neoplastic and radiosensitizing activities of FTIs appear to be mediated, at least in part, by switching the balance from RhoB-F to RhoB-GG (40, 41, 92, 93). The preliminary data suggested that knockdown of RhoB mimicked the effects of FTIs. It impaired growth and survival of GSCs and made them highly sensitive to GSIs while irresponsive to FTIs, suggesting that loss of RhoB-F rather than gain of RhoB-GG has important roles in GSCs. As CD133− non-stem GBM cells were not sensitive to FTIs (data not shown), the present inventor will compare the expression levels as well as the activation status of RhoB between these two subpopulations. The present inventor will also validate the hypothesis that RhoB is the primary target of FTIs in GSCs through rescue experiments. First, the present inventor will determine if a constitutively active RhoB mutant, Myr-RhoBV14 (91), renders GSCs resistant to the growth inhibitory and radiosensitizing effects of FTIs. Second, the last four amino acid residues of RhoB can be modified so that the mutants are either exclusively modified by farnesylation (RhoB-F) or geranylgeranylation (RhoB-GG). The functions of the RhoB-F and RhoB-GG mutants in GSCs and their ability to rescue cells from loss of wild type RhoB will be assessed. Finally, the present inventor will determine how these mutants interact with GSI treatment or Notch activation.

Determine the In Vivo Efficacy of GSI and FTI Combination±Radiation Using an Orthotopic GBM Model.

The in vitro results showed that combination of GSI and FTI synergistically inhibited growth and survival in GSCs following radiation, suggesting that it may improve the efficacy of radiotherapy in vivo. The complexity of tumor environment and its impacts on tumor response to the proposed treatments must be rigorously evaluated under physiologically relevant conditions. The present inventor will therefore examine this hypothesis using an orthotopic tumor model. The in vivo assays will use RO4929097 (GSI) and Tipifarnib (FTI) that are currently in phase II trials for GBM treatment. Overall survival will be the primary endpoint. Acute tumor response will be assessed the next day after completion of treatments by IHC, flow cytometry and immunoblotting.

The treatment plan is as follows. Following intracranial implantation of $2\times10^5$ GBM cells, animals will be maintained for 15 days to allow establishment of tumors, as determined in the previous studies (3, 18, 34). Xenograft-bearing mice will be treated with orally administered 30 mg/kg/day RO4929097 and/or 50 mg/kg/day Tipifarnib for 7 consecutive days modified from published protocols (94, 95). Four hours after the initial drug administration, animals will receive local X-ray radiation for 5 consecutive days of 2 Gy/day (10 Gy in total) modified from previous study (70). To analyze the acute tumor response to treatments, two mice per arm will be sacrificed 1 day after completion of all treatments. One brain will be fixed for IHC and H&E staining Brain sections will be stained for Ki67 (proliferation), vWF, CD31 (vessel density), phospho-S473-Akt, cleaved caspase-3 (apoptosis), CD133 and nestin (stem cell markers). The other tumor is resected, half is lysed for immunoblotting and half is enzymatically dissociated for flow cytometry analysis of the percentage of CD133+ tumor cells. The rest of 8 mice in each arm will be maintained until development of neurological signs or for 120 days. At the endpoint of the experiments, all remaining mice will be euthanized and be subjected to histological processing.

Expected Results and Analysis:

The preliminary results suggest that GSIs and FTIs synergistically target GSCs, in large part through inhibiting Notch and RhoB, respectively. Experiments are therefore designed to systematically assess the potential of this novel combination for GBM treatment. On the basis of the preliminary observations, it is expected that this combination will significantly prolong survival of xenograft-bearing animals. Interpretation of tumor response to treatment can be complex. Overall survival will be the primary endpoint. Survival of GSCs shortly after completion of treatments will be another focus. Bao and Rich have demonstrated that the percentage of CD133+ GBM cells increased in cultures as well as in GBM xenografts following radiation (3). It is anticipated that the ratio of CD133+ cells in tumors treated with GSIs or FTIs, particularly the combination, will be significantly lower than tumors treated by radiation alone. Expression of additional cancer stem cell markers can be analyzed by IHC staining, immunoblotting and flow cytometry (84). Observation of stronger inhibition of the RTK/Ras/Akt pathway in treated tumors is also expected. Additionally, Notch signaling has important role in angiogenesis (96, 97), therefore the blood vessel density in tumors after treatment will be analyzed. However, the focus will be given to survival of GSCs as well as non-stem cancer cells, as it is contemplated that effective killing of GSCs may be critical for sustained tumor control.

Potential Alternatives:

One question is whether the drugs can efficiently inhibit their target according to the proposed doses. As both RO4929097 and Tipifarnib have been studied in mouse xenograft models, the present inventor will start with the published doses and administration route (oral gavage) (94, 95). While the efficacy of Tipifarnib in CNS has been well described (98), whether RO4929097 can be efficiently delivered through the blood-brain barrier remains to be determined (94), therefore will be determined by pilot tests. After drug administration (8 and 24 hours), the present inventor will collect the xenograft tumors and immunoblot the levels of cleaved Notch1 as the marker of Notch inhibition and the levels of farnesylated HDJ-2 as the marker of farnesyltransferase inhibition (99). If RO4929097 at proposed dose cannot effectively inhibit Notch1 activation in intracranial xenografts, the present inventor will increase to 60 mg/kg/day, the highest reported dose. Other GSIs that have been tested in CNS, such as MK-0752, can also be used (100). Alternatively, Notch signaling could be genetically targeted by a lentiviral vector directing inducible expression of shRNA (pTRIPZ, Open Biosystems) Inhibition of Notch can be induced by activating the Tet-On promoter 24 hours prior to radiation starts. The impact of RhoB knockdown in GBM can be assessed by a similar strategy. These experiments will validate the results obtained by chemical inhibition.

Determine Whether GBM-Associated Genomic Aberrations May Determine Tumor Response to Notch-Targeted Combination Therapy.

Figure 4:
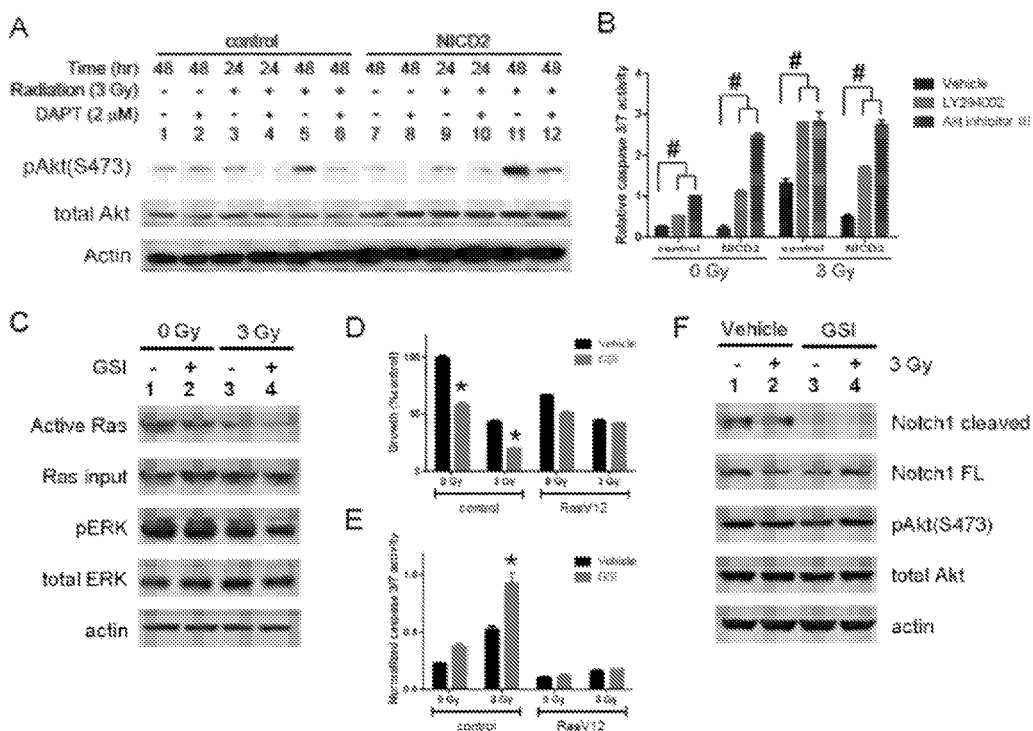
FIG. 4 shows that Notch regulates the Ras/PI3K/Akt pathway in GSCs. (A) T4302 CD133+ cells were infected with NICD2-lentivirus and treated with 2 µM DAPT±3 Gy radiation. Cells were collected at 24 or 48 hours after treatment. Protein levels of phospho-s473 Akt, total Akt and actin were blotted. (B) Control CD133+ cells or NICD2-expressing cells were pre-treated with 10 µM PI3K inhibitor (LY294002), or 50 µM Akt inhibitor (SH-6) for 4 hours prior to radiation. Relative caspase 3/7 activity was determined at 48 hours after radiation as described in FIG. 3C. (C) T4302 CD133+ cells were treated with 200 nM RO4929097 (GSI)±3 Gy. Active Ras levels were determined by a Ras Pull Down Assay kit using a pan-Ras antibody (Pierce). (D, E) T4302 cells were infected with H-Ras V12-lentivirus. Cells were treated with 200 nM RO4929097 (GSI)±3 Gy. Growth of cells was determined at day 5 after treatment (CellTiter-Glo assay, Promega). Relative caspase 3/7 activity was determined at 48 hours after treatment. (F) H-Ras V12-expressing T4302 CD133+ cells were treated as described in FIG. 4C. Equal amounts of protein were resolved by SDS-PAGE and analyzed by immunoblotting with indicated antibodies. *: $p<0.05$ by Student's t-test.
Figure 8:
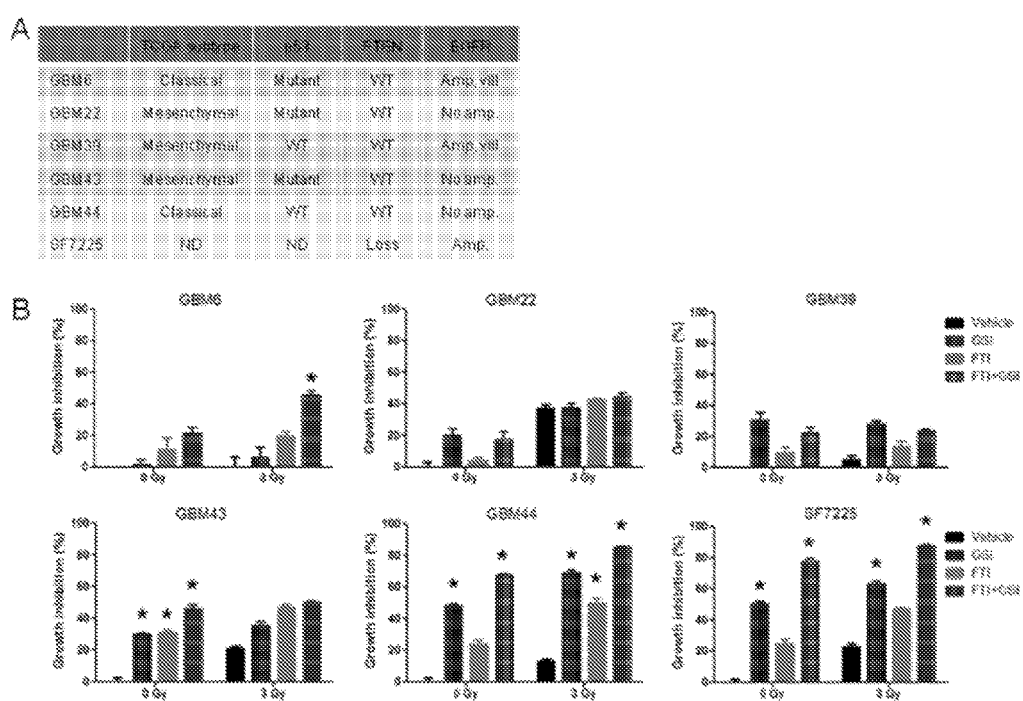
FIG. 8 shows a differential response of GBM tumors to GSIs, FTIs and/or radiation. (A) Known genetic features of selected GBM samples. WT: wild type; Amp: amplification; vIII: EGFRvIII; ND: not determined. (B) Spheroid GBM cultures were derived from freshly collected subcutaneous tumors and cultured for 2 weeks in stem cell media to enrich stem cell-like cancer cells. SF7225 was maintained as a primary spheroid culture. Growth inhibition at day 5 after treatment was determined as described in FIG. 5. *: $p<0.01$ by Student's t-test and growth inhibition ≥30% vs. the corresponding vehicle-treated groups. #: $p<0.01$ and >30% growth inhibition vs. the radiation only groups.
Figure 10:
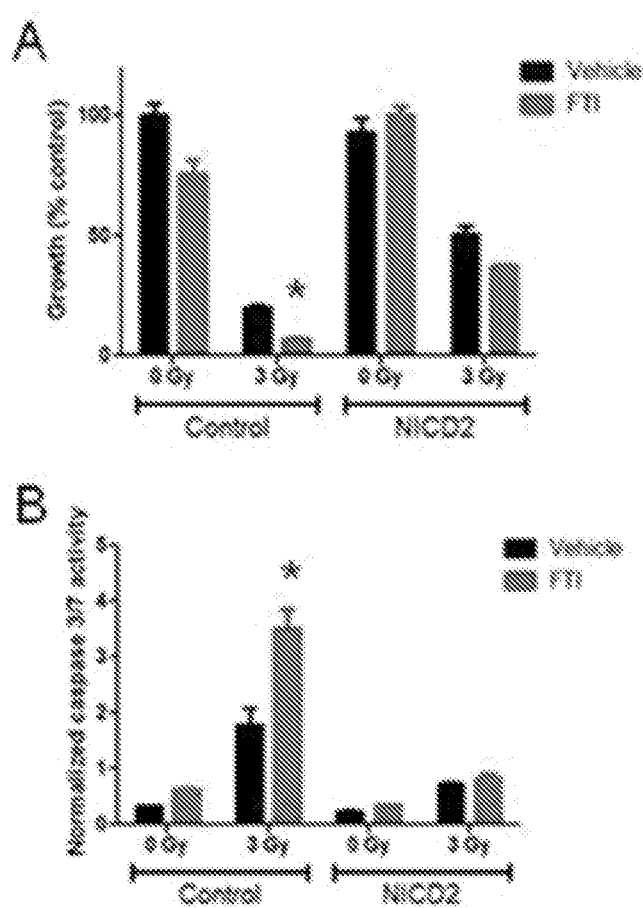
FIGS. 10A and 10B show activation of Notch conferred resistance to farnesyltransferase inhibitors. T4302 CD133+ cells were infected by control lentivirus or lentivirus directing expression of a constitutively active mutant of Notch2 (NICD2) and selected by 1 µg/ml puromycin. Cells were treated with DMSO (vehicle) or 100 nM Tipifarnib (FTI)±3 Gy. Cell growth (FIG. 10A) and caspase activation (FIG. 10B) were determined as described in FIG. 1. *: $p<0.001$ by Student's t-test.

Rationale:

It has been well recognized that tumor response to targeted therapy varies dramatically. The diverse therapeutic response is largely because human tumors are highly heterogeneous at molecular levels, even within the same pathological category. Recent advances in genome-wide association studies (GWAS), exemplified by the Cancer Genome Atlas (TCGA) project, have generated an overarching view of the genomic aberrations of GBM and identified several molecular subtypes that differ in their sensitivity to the standard radio-chemotherapy (53-57). The majority of recurrent aberrations identified in GBM can be categorized into two functional groups. The first group inactivates the key tumor surveillance mechanisms by deleting or inactivating TP53, Rb, p16INK4A and p14ARF. Another set of aberrations collectively lead to hyperactivation of the RTK/Ras/PI3K/Akt pathway by either loss-of-function of PTEN/NF1 or gain-of-function of EGFR, PDGFR, Met, and PI3K. Interestingly, this pathway appears to be regulated by Notch and can be targeted by a combination of GSI and FTI. This raises one important question whether the mutational status of this pathway may affect tumor response to the combination therapy. Additionally, upregulation of Notch signaling components, such as Jag1 and Notch3, are associated with poor prognosis in GBM (FIG. 2). It remains to be determined if overexpression of these genes correlate with tumor dependence on Notch activity. Several groups including the present inventor's laboratory recently interrogated the role of Notch in GBM and reported different sensitivities (35-37, 101). Additionally, the preliminary data suggest that activation of the Notch/RTK/Ras/Akt pathway by expression of activating mutants, such as NICD2, H-RasV12 or Myr-Akt1, confer resistance to GSIs, as well as its combination with FTIs (FIG. 4, 10, and data not shown). However, these mutants have not been identified in GBM patients, therefore more physiologically relevant models are needed. Using neurosphere cultures derived from a collection of genetically heterogeneous GBM xenograft tumors, it has been shown that tumors significantly differed in their response to GSI, FTI, radiation, alone or in combinations (FIGS. 8 and 10). A panel of 35 GBM tumors has been collected from independent sources and will be continuously expanded by the present inventor's laboratory with new samples derived from de-identified patient specimens provided by the Molecular Neurosurgical Tissue Bank. Utilizing this GBM test panel that mimics human tumor heterogeneity, the present inventor will explore candidate biomarkers that may predict tumor response to Notch-targeted combination therapy.

Determine tumor response to the combination treatment of GSI, FTI and/or radiation in a panel of molecularly characterized GBM xenograft tumors. Subcutaneous GBM xenografts preserve important GBM biological and molecular features, such as EGFR amplification that is often lost in established cell lines (69, 70, 102). Recently, the TCGA study showed that GBM tumors could be classified on the basis of an expression signature generated from clinical specimens, but established cell lines could not be classified in this manner (57), suggesting that GBM tumors also preserve the molecular heterogeneity of original tumors. On the basis of the GBM panel, the present inventor will first determine response to GSI, FTI, and/or radiation using spheroid cultures derived from freshly collected xenograft tumors. The primary endpoint for response will be growth inhibition at day 5, and the secondary measurement will be the neurosphere-forming capacity, or colony formation if cells grow in monolayer, as described in the previous study (34, 84). As described in FIG. 8, a greater than 30% inhibition of growth or neurosphere formation by GSI and/or FTI (up to 3 µM) is defined as positive response. Following 3-Gy radiation, if the inhibition remains >30% (treated+3 Gy vs. sham-treated+3 Gy), the effects of the drugs are regards as radiosensitizing. Radiation dose will be decreased if 3 Gy alone induced too much growth inhibition. Such response will be validated in vivo using representative samples according to methods described in specific aim 2.

Tumor Samples:

GBM samples used in the study were collected from three independent sources. First, a set of 24 GBM tumors were provided by Dr. Sarkaria at Mayo Clinic. These tumors were serially passaged as subcutaneous xenografts and recapitulate typical GBM pathology when implanted intracranially (69, 70, 102, 103). According to the TCGA classification, these tumors belong to proneural (5 tumors), classical (12 tumors), and mesenchymal (7 tumors) subtypes (57). Expression patterns, gene copy numbers, and mutational status of several key GBM genes, such as EGFR, TP53, and PTEN, have been characterized for these samples (104). Second, more than 15 GBM tumors have been generated in Dr. Jeremy Rich's laboratory with the CD133+ subpopulation has been characterized (14, 34, 84, 85). Last, additional GBM xenografts and primary cultures are derived from surgical specimens available at the Vanderbilt Molecular Neurosurgical Tissue Bank in collaboration with Dr. Michael Cooper and Dr. Reid Thompson. In this regard, two primary cultures have been generated with matched xenograft tumors for comparison. All tumors will be characterized at molecular levels as described below, and serially passaged as flank subcutaneous xenografts for sustained supply of materials for proposed experiments. Overall, it is planned to establish and characterize a panel of more than 50 molecularly characterized GBM xenograft tumors during the funding period.

Determine if a Molecular Signature May Predict Tumor Response to Notch-Targeted Combination Therapy.

Personalized medicine for GBM is still in its infancy. One important step towards this direction is the finding that the methylation of MGMT promoter can predict favorable patient response to temozolomide (105, 106). Recent GWAS studies including the TCGA project have identified a panel of molecular alterations that are critically implicated in GBM biology and differentially presented in GBM tumors, including upregulation of Notch pathway components (55, 57). These studies have generated an important framework to understand the impacts of cancer genome on clinic outcomes. For all GBM samples utilized in this proposed study, expression profiles and genomic aberrations will be characterized with a focus on molecular events that may alter RhoB, Notch and the RTK/Ras/PI3K/Akt pathway (Table 1). Tumor response will be correlated with genomic aberrations, protein levels, as well as protein phosphorylation status as surrogates for pathway activity. The predictive power of individual variables will then be determined, as well as a signature that combines multiple candidate markers, which will in turn be validated by genetic approaches.

Molecular Characterization:

RNA samples will be harvested from freshly collected xenografts, and DNA samples will be extracted from cultured tumor cells. Gene expression profiles and point mutations will be determined by RNA-seq. The RNA-seq technology was selected because its cost at the present inventor's institution is now markedly lower than the addition of microarray and targeted genome shotgun sequencing. Gene copy number will be assessed by array CGH (comparative genomic hybridization) using the Affymetrix SNP 6.0 arrays. Genomic analysis will be completed by the Vanderbilt Functional Genomics Share Resource. Additionally, protein levels and phosphorylation status of several key molecules implicated in this Notch-regulated signaling network will be determined in cultured spheres as well as in xenograft tumors.

Statistical Analysis:

Statistical analysis will be performed by the Cancer Biostatistics Center at Vanderbilt-Ingram Cancer Center. The endpoint of the study, tumor response, will be reported by two types of measurements, either on a dichotomous scale, i.e. sensitive or resistant; or on a continuous scale, e.g. growth inhibition. To assess the primary hypothesis that the candidate biomarkers, singularly or jointly, has the ability to predict the tumor response, the goal is to create a prediction model using a subset of the candidate biomarkers (summarized in Table 1). It has been demonstrated that regression shrinkage and subset selection via lasso method improve model interpretation and prediction accuracy (107). Analysis will be carried out by lasso method as following: (a) When outcome variable is measured on a dichotomous scale, prediction model will be built using multivariate logistic regression method through lasso procedure to evaluate if these biomarkers in combination has desirable ability in predicting tumor response types. The final model derived by lasso method will be further internally validated using the training data set described in this proposal. A bias-corrected estimate of prediction accuracy was obtained by the bootstrap validation method. The tumor response classification prediction performance will be assessed by a widely used measurement of diagnostic discrimination: the area under receiver operating characteristic (ROC) curve (108). (b) When outcome variable is measured on a continuous scale, the prediction model will be built by applying multiple linear regression method, also through lasso procedure. Mean square error will be calculated to evaluate how well the regression model fits the data. In addition, R-square will be used to evaluate the goodness-of-fit of the proposed regression model. Similarly, the final model will be internally validated by bootstrap method to provide bias-corrected estimates of mean square error and R-square. The lasso implementation of regression methods, either logistic regression or linear regression from Friedman, Hastie and Tibshirani available through the R package glmnet will be adapted accordingly to build the proposed prediction model (109).

Figure 9:
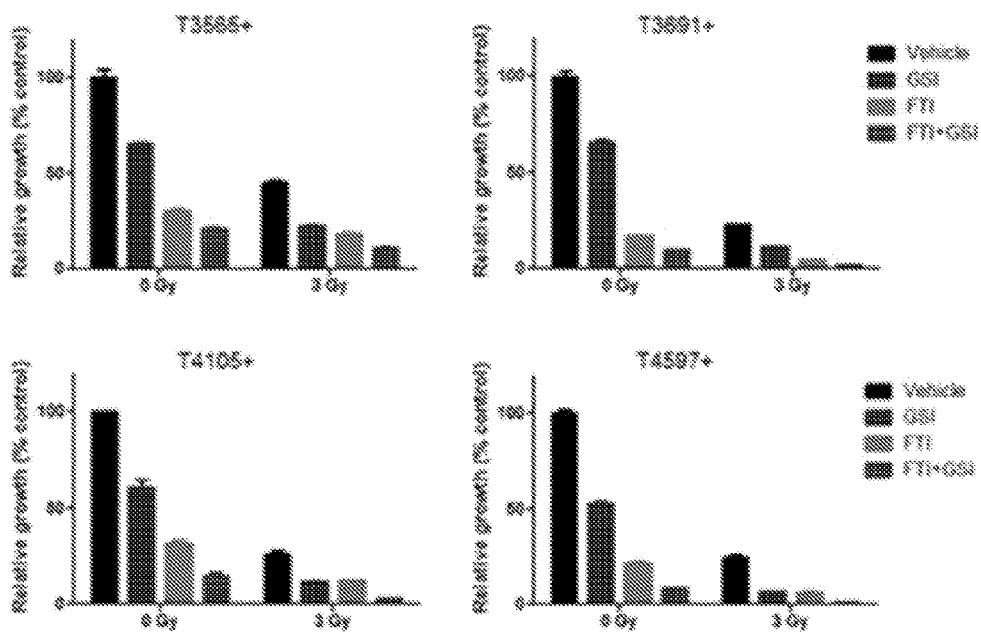
FIG. 9 shows the combination effects of GSIs and FTIs in different glioblastoma stem cells. CD133+ cells were derived from multiple glioblastoma xenograft samples as indicated. The growth inhibitory effects by GSI and/or FTIs were determined as described in FIG. 5.

GTPase activities as well as other proteins that are regulated by farnesylation. This combination treatment potently decreased growth and survival of CD133+ GBM stem cells in culture (FIGS. 8 and 9).

GBM stem cells are thought to be the primary driving force of tumor propagation and recurrence and also demonstrate stronger resistance to radiotherapy than bulk tumor cells. Therefore, effective killing of GBM stem cells may delay or even prevent tumor recurrence. Using a panel of glioblastoma xenograft samples, it was demonstrated that within a 5-day period, gamma-secretase inhibitors (RO4929097) or farnesyltransferase inhibitors (tipifarnib) alone achieved about 50-70% growth inhibition relative to the sham-treated groups. In combination with radiation, GSIs or FTIs alone reduced cell numbers by ~75%. The combination of these two agents plus radiation resulted in >90% growth inhibition (FIG. 5A and FIG. 9).

As the combination of GSIs and FTIs demonstrated greater-than-additive effects, whether these two compounds have synergistic effects using the Chou-Talalay method was assessed. Except a few data points for drug concentration <5 nM, the combination index values of RO4929097 (GSI) and tipifarnib (FTI) on growth inhibition of GSCs were substantially lower than 1, indicating synergistic effects (FIGS. 5D and 5E). Additionally, this synergistic interaction appeared to be radiation independent.

It was further shown that the combination of GSIs and FTIs, in the presence of ionizing radiation, resulted in stron-

TABLE 1

GBM associated molecular aberrations that may be implicated in tumor response to the GSI/FTI combination therapy. Yes: the molecular event will be rigorously analyzed and correlated with tumor response.

|  | Notch elements | RhoB | EGFR | PDFGFRA | MET | TP53 | NF1 | PTEN | PIK3R/ PIK3CA | AKT |
|---|---|---|---|---|---|---|---|---|---|---|
| Expression | Yes | Yes | Yes | Yes | Yes | Yes | Yes | Yes | Yes | Yes |
| Mutation |  |  | Yes | Yes |  | Yes | Yes | Yes | Yes |  |
| Amplification |  |  | Yes | Yes | Yes |  |  |  |  |  |
| Deletion |  |  |  |  |  |  | Yes | Yes |  |  |
| Phosphorylation |  |  | Yes | Yes | Yes |  |  |  | Yes | Yes |

Expected Results and Analysis:

Mutations may not only confer resistance to agents inhibiting the mutated targets, but also their upstream regulators. For example, K-Ras mutations are associated with resistance to EGFR inhibitors in colorectal and lung cancer (68). On the basis of the preliminary understanding of the Notch-regulated radioprotective mechanism, it is reasonable to speculate that tumors harboring PTEN loss or PI3K mutations may show significant resistance to GSIs and combinations, whereas mutations altering Ras activity, such as EGFR amplification, may confer partial resistance via signal compensation. Additionally, tumors with higher levels of Notch signaling elements may show stronger response. Nevertheless, results of the experiments proposed in this aim require rigorous statistical analysis, as well as validation in vitro and in vivo by genetic targeting approaches.

Example 2

Figure 7:
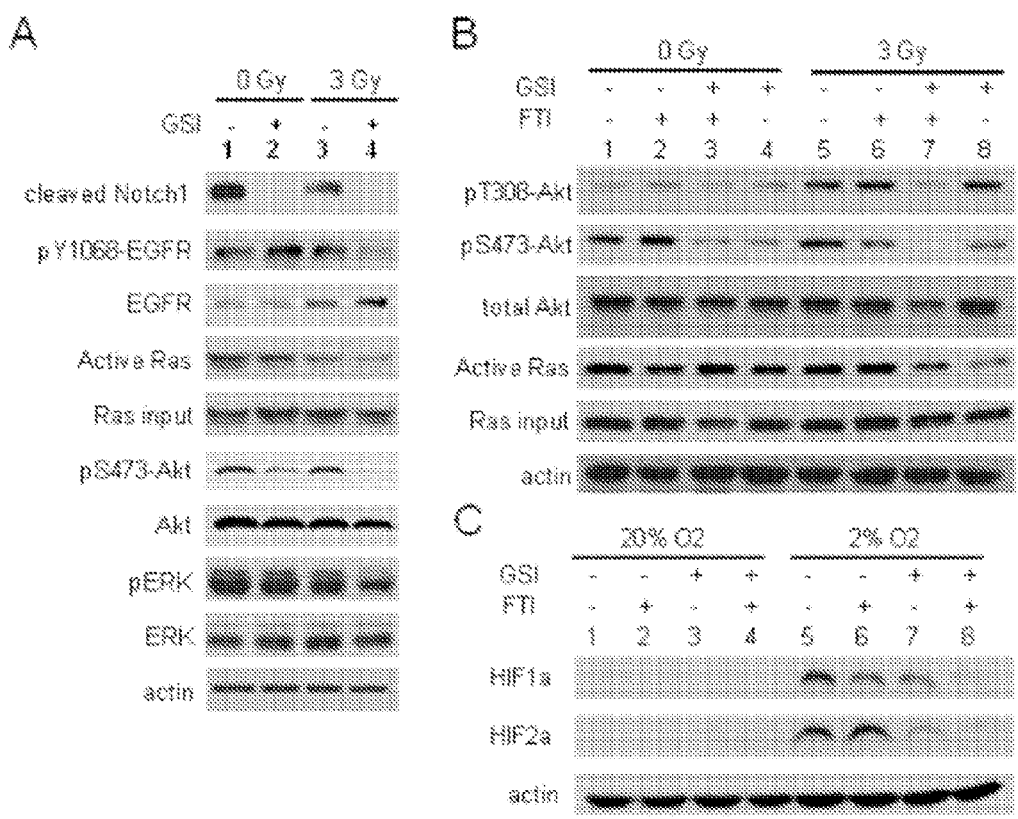
FIG. 7 shows that the combination of GSIs and FTIs results in potent inhibition of EGFR, Akt and HIF1α/2α. (A) T4302 CD133+ cells were treated with 200 nM RO4929097 (GSI), and irradiated 4 hours later. Cells were cultured for two days and lysed for immunoblotting. (B) T4302 CD133+ cells were treated with 200 nM GSI or FTI±radiation. Cells were lysed 2 days after treatment. (C) T4302 CD133+ cells were treated with 200 nM GSI±FTI for 24 hours, and left under normoxia or in 2% O2 for 16 hours before being lysed for immunoblotting.

On the basis of a Notch-targeted therapy recently reported by the present inventor's laboratory and other groups, a novel combination therapy was developed and is described herein, which can include ionizing radiation, gamma-secretase inhibitors (GSIs) that block Notch signaling, and farnesyl-transferase inhibitors (FTIs) that attenuate Ras and Rho ger inhibition of Akt activity than single agent, as suggested by weaker phosphorylation at the threonine 308 and serine 473 residues of Akt1 (FIG. 7). This potent inhibition of Akt may contribute to the growth and survival inhibitory effects of this combination treatment. Finally, it was found that constitutive activation of Notch signaling rendered GSCs resistant to FTI-treatment (FIG. 10), suggesting the key targets of GSIs and FTIs are regulated by a Notch-dependent signaling network.

Example 3

The present inventor has now identified a synergistic drug combination of farnesyl-transferase inhibitors (FTIs) and γ-secretase inhibitors (GSIs) that target Notch signaling. The combination of FTIs and GSIs synergistically decreased growth, survival, neurosphere formation, and radioresistance of GSCs. In contrast, GSIs and FTIs, singly or in combination, had limited impacts on non-stem GBM cells. Notably, this drug combination repressed orthotopic GBM development more effectively than either agent alone, with or without radiation. Of particular interest, a combination of RO4929097 (GSI), tipifarnib (FTI) and radiation appeared to achieve sustained control of orthotopic GBM in 2 out of 7 experimental mice. The data further suggested that Notch-dependent activation of the EGFR/Ras/Akt signaling axis played important roles in the radioresistant phenotype observed in GSCs. The synergistic interaction of GSIs and FTIs appeared to be mediated by combinatorial inhibition of Akt and HIF1α/HIF2α. These findings have been validated in cells derived from several primary GBM xenograft lines and by multiple GSIs and FTIs. Taken together, the findings lay the foundation to translate the GSI and FTI combination as novel therapeutic tools and radiosensitizing approaches for GBM treatment.

Results

GSIs and FTIs Synergistically Target GSCs and Repress Orthotopic GBM Tumor Development.

Figure 11:
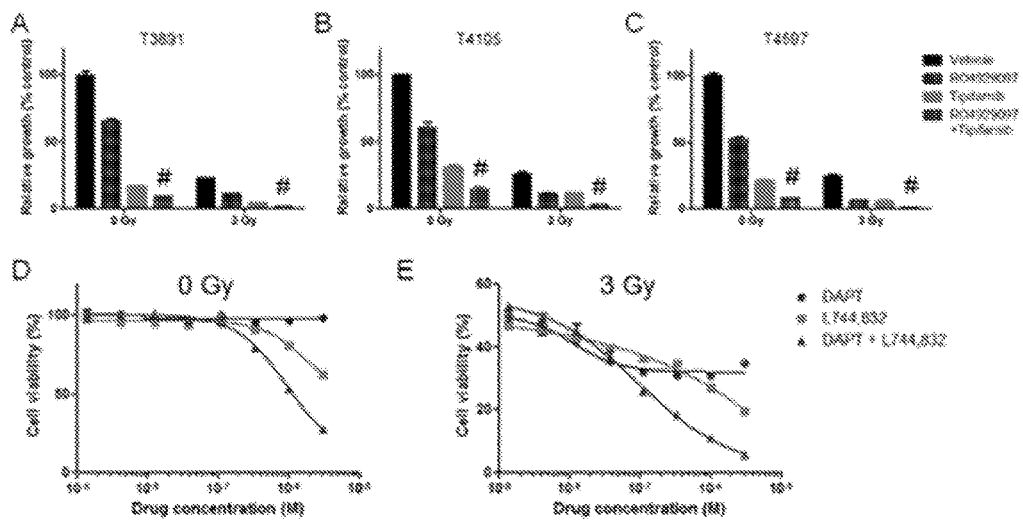
FIG. 11 shows that compositions including different combinations of gamma-secretase inhibitors (GSIs) and farnesyl transferase inhibitors (FTIs) synergistically repress GSC growth and survival in different GBM samples. (A to C) Relative growth of CD133+ cells derived from T3691, T4105, T4597 GBM primary xenograft lines on day 5 was determined as described in FIG. 5. #: $p<0.001$ by one-way ANOVA, combo vs. single agents. (D,E) The combinatorial effects of DAPT (GSI) and L744,832 (FTI) on viability of T4105 CD133+ cells were determined as described in FIGS. 5D and 5E.

The present inventor has shown that GSIs significantly impaired self-renewal and viability of GSCs through inhibiting the Notch pathway (34). However, despite treatment with GSIs plus radiation, a substantial percentage of GSCs remain viable and tumorigenic (34). To achieve more effective eradication of GSCs, the present inventor has begun to explore agents that would augment the radiosensitizing effects of GSIs. FTIs were selected due to its activities targeting Ras and Akt and its proven clinical safety and brain penetrating potential (39, 44). Here, it is demonstrated that FTIs synergistically enhanced the ability of GSIs to repress the growth, self-renewal, survival and radioresistance of GSCs derived from multiple GBM primary xenograft lines (FIG. 5). In the absence of radiation, the combination of a GSI (RO4929097) and an FTI (tipifarnib) reduced T4302 CD133+ cell numbers by approximately 70% after 5 days of treatment (FIG. 5A) and induced significant activation of caspase-3/-7 (FIG. 5B). In comparison, GSI or FTI alone resulted in weaker growth inhibition without apparent activation of apoptosis (FIGS. 5A and 5B). The combination of GSI and FTI also led to more potent inhibition of cellular proliferation and survival following radiation (FIGS. 5A and 5B). Particularly, a combination of GSI, FTI, and radiation reduced cell numbers by approximately 95% after 5 days of treatment (FIG. 5A). In contrast, T4302 CD133− cells were largely insensitive to GSIs and/or FTIs (FIG. 5C). As the combination of GSI and FTI demonstrated potentially greater-than-additive effects against GSCs, it was assessed if the combination of these two compounds was synergistic against GSCs using the Chou-Talalay method (66). In a dose-response assay, except at drug concentrations below 5 nM, the combination index (CI) values for GSI and FTI on inhibition of cell viability were significantly lower than 1, indicating synergism of this drug combination (see the right-hand Y axis, FIGS. 5D and 5E). The drug combination also synergistically inhibited neurosphere formation of T4302 CD133+ cells (FIG. 5F). Similar results have been validated in more than 5 different GSCs (FIG. 9, FIG. 11 and data not shown) and using additional GSIs (e.g. DAPT) and FTIs (e.g. L744,832) (FIGS. 11D and 11E). It is anticipated that other GSIs, such as MK-0752 and compound E, will have similar effects.

The Combination of GSI and FTI Represses Orthotopic GBM Tumor Development.

Figure 12:
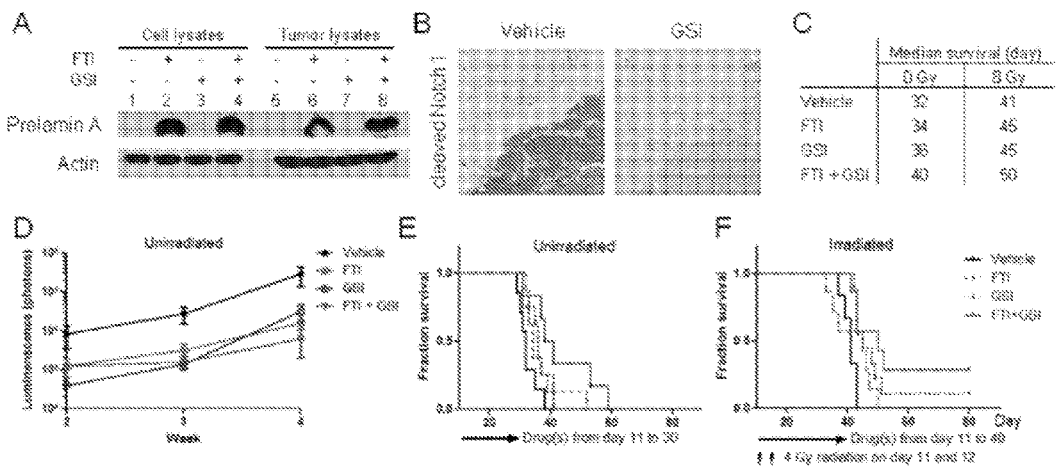
FIG. 12 shows that compositions including a combination of gamma-secretase inhibitors (GSIs) and farnesyl transferase inhibitors (FTIs) repress orthotopic GBM growth. (A, B) T4302 CD133+ cells were treated with 100 nM GSI±FTI for 48 hours and lysed in RIPA buffer. Mice bearing intracranial T4302 tumors were orally treated with 30 mg/kg/day GSI once a day (q.d.)±100 mg/kg/day FTI twice a day (b.i.d.) for 7 days. Brains were resected and homogenized in RIPA buffer. All lysates were blotted with an antibody specific to prelamin A. (B) Additional brains were fixed and resected for IHC staining for cleaved Notch1. (C) T4302 CD133+ cells were infected with lentivirus expressing firefly luciferase and selected with puromycin for two days. Athymic nude mice were intracranially implanted with 5,000 cells, maintained for 10 days, and treated with GSI±FTI for 20 days as described above. In a separated experiment, animals were treated by the same protocol, except they were given 2 doses of 4 Gy X-ray irradiation on day 11 and day 12, 4 hours after drug administration. These mice were on drugs for 30 days. The median survival was calculated by the GraphPad Prism 5 software. (D) Animals in the unirradiated experiment were tracked for their tumor progression by bioluminescence imaging. The Y axis is set in a log scale. (E,F) The survival curves of these two experiments are shown.

On the basis of the synergistic interaction between GSIs and FTIs observed in vitro, the present inventor next assessed whether this drug combination was more potent than single agents in vivo. We chose RO4929097 (GSI) and tipifarnib (FTI) as the compounds for the in vivo study because both have been tested in human subjects and tipifarnib has shown some efficacy in a phase II GBM trial (47,111). In a feasibility test, it was demonstrated that tipifarnib significantly increased accumulation of prelamin A in intracranial tumors (FIG. 12A). Accumulation of this precursor protein indicates inhibition of farnesyltransferase, which is required for processing of prelamin A (112). We also showed that RO4929097 decreased the levels of cleaved Notch1 in intracranial tumors as shown by immunohistochemical staining (IHC), suggesting its penetration into the brain (FIG. 12B). The combination of RO4929097 and tipifarnib extended median survival from 32 days to 40 days (p=0.018 as calculated by the log-rank test) (FIGS. 12C and 12E). In comparison, GSI or FTI alone did not produce significant benefits. Bioluminescence imaging showed drastic differences in tumor size between the treated groups and the control group during the course of treatment (FIG. 12D). In a separate experiment, animals were given 2 doses of 4 Gy local X-ray irradiation on the first and second day of treatment, 4 hours after drug administration. The drug combination again significantly extended animal survival (p=0.013). GSI showed some modest effects while FTI alone had no significant effects (FIGS. 12C and 12F). Of particular interest, 2 out of 7 mice in the arm treated with the drug combination plus radiation appeared to be free of tumor burden as of now (~day 80), as suggested by the absence of weight loss or any other visible symptoms. In addition, 1 out of 8 mice in the GSI+IR-treated arm also appeared to be free of tumor burden. These mice will be kept for up to 120 days and sacrificed for histological analysis to confirm the absence of residual tumors. Take together, these data suggest that the GSI and FTI combination has more potent therapeutic potential than either drug alone for GBM treatment in vitro as well as in vivo.

GSIs and FTIs Converge on Akt and HIF1/2.

The published studies have shown that Akt critically mediated the Notch-dependent radioprotective functions (34). We have since then found that Notch inhibition by GSIs decreased levels of phosphorylated EGFR and GTP-bound active Ras in a radiation-dependent manner (FIG. 7A). In addition, GSI induced stronger Akt inhibition in irradiated cells than in unirradiated cells (FIG. 7A). To determine the mechanisms through which GSIs and FTIs synergistically target GSCs, it was first assessed the impact of this drug combination on the EGFR/Ras/Akt axis. The preliminary results suggested that the combination resulted in a stronger inhibition of Akt activity than either drug alone as shown by decreased phosphorylation at both serine 473 and threonine 308 (FIG. 7B). Because the HIF transcriptional factors are known to cooperate with Notch to regulate normal stem cell biology (87, 113, 114), the impacts of GSIs and FTIs on HIF regulation was also assessed. Remarkably, it was found that while either RO4929097 or tipifarnib alone resulted in a moderate reduction of HIF1α and HIF2α levels upon hypoxia stimulation, the combination led to a significantly more potent inhibition of both HIF proteins (FIG. 7C). The instrumental role of the hypoxia response critically mediated by stabilization of HIF1α/2α has been well established in cancer biology and radiation oncology (115, 116). Eyler and colleagues recently also reported the essential functions of HIF1α and HIF2α in GSCs (117). Knockdown of these two genes results in loss of proliferation and cell viability even under normoxic conditions (117). However, development of small molecule HIF inhibitors has proven to be difficult, and only a few are in preclinical and early clinical development (118). The findings that GSIs and FTIs may interfere with HIF induction under hypoxia have significant clinical implications and warrant further investigation.

Materials and Methods

Reagents and GBM Samples:

Compounds for in vitro experiments were purchased from Selleckchem, Houston, Calif. For in vivo experiments, RO4929097 was provided by Roche, and tipifarnib was provided by Johnson and Johnson. GBM samples used in the studies are originally derived from surgical specimens and maintained as serially passaged subcutaneous xenografts lines. This model has been increasingly used by the brain tumor research field, because they preserve the GSC subpopulation and maintain the original tumor phenotypes and genotypes, thus representing a physiologically relevant model for basic and translational research (119, 12). These lines were established by Dr. Jeremy Rich at Cleveland Clinic.

Enrichment and Culture of GBM Stem Cells:

Tumor cells are enzymatically dissociated from freshly collected subcutaneous xenograft tumors and cultured overnight before sorting. The CD133− and CD133+ fractions are separated either by magnetic sorting using the CD133 Microbead kit (Miltenyi Biotech), or labeled with APC-conjugated CD133 antibody (Miltenyi Biotech) and sorted by flow cytometry. CD133+ cells are maintained in neurobasal media supplemented with 2% B-27, 20 ng/ml EGF, and 20 ng/ml bFGF. CD133− cells are maintained in DMEM supplemented with 10% FBS but are changed into stem cell media at least 24 hours prior to experiments to control differences in cell media. To reduce the impact of prolonged culture, both CD133+ GSCs and CD133− non-stem GBM cells are maintained for less than 5 passages in culture before disposal. New batches of cells will be isolated from freshly collected tumors. Because both CD133+ and CD133− cells are difficult to transfect, all genetic modifications will be performed with lentiviruses.

Neurosphere Formation (Clonogenic Survival):

The floating neurosphere culture system was initially established by Reynolds and Weiss to maintain adult neural progenitors in vitro (120), and was later adapted for GSC culture (11, 12). Neurospheres can be counted in a manner similar as regular colony formation assays. CD133+ cells were dissociated into single cells, plated in 24-well plates at 100 cells per well, and treated as indicated. Cells were cultured for 10 days before spheres more than 50 cells were counted.

Cell Viability Assay:

GSC sensitivity to drug(s) was primarily measured as inhibition of cell viability (survival). Cells were treated with drugs alone or in combination±3-Gy radiation at indicated concentrations. Cell viability is determined by CellTiter-Glo kit (Promega) after 5-day incubation. $IC_{50}$ values are calculated by the GraphPad Prism5 software.

Animal Assays:

Mice were first anesthetized using an isoflurane inhalation system and maintained on the nose cone during the procedure. 5,000 CD 133+ GSC cells suspended in 10 µl PBS were implanted into the right cerebrum with 30 gauge needles. Animals were maintained for 10 days to allow tumor establishment. Before treatment, any mouse showing distress or neurological signs (e.g. lethargy, hemiparesis, ataxia, seizures) would be euthanized. The remaining mice will be randomized to treatment groups just prior to treatment. Tumor-bearing mice received 30 mg/kg RO4929097 (GSI) once a day (q.d.) and/or 100 mg/kg tipifarnib (FTI) twice a day (b.i.d.) via oral gavage for 20 days in the absence of radiation or 30 days in the irradiated groups. Four hours after the initial drug administration, animals received local X-ray radiation at 2 fractions of 4 Gy per day for 2 consecutive days (8 Gy in total). Animals were immobilized in a plastic restraint, exposed to X-ray radiation delivered by a Pantak X-ray irradiator, while the remainder of the body is shielded with lead.

Mice were weighted and visually inspected daily once treatments begin. Tumor development was monitored by bioluminescence imaging every week. Animals are anesthetized with 3% isoflurane and intraperitoneally injected with 100 µl of 30 mg/ml potassium D-luciferin salt dissolved in PBS each mouse (weights at 20-30 grams). Ten minutes after injection of luciferin, animals are imaged using a Xengogen IVIS 200 imaging system. The primary readout of the in vivo tests is the median survival calculated by the Kaplan-Meier estimator using the GraphPad Prism5 software. Drug efficacy was also be assessed by tumor sizes estimated by bioluminescence imaging.

Statistical Considerations:

P value will be calculated by ANOVA comparison or Student's t-test using the GraphPad Prism5 software. P values less than 0.05 will be considered significant. All data points will be repeated at least in triplicate for each experiment.

Throughout this document, various references are mentioned. All such references are incorporated herein by reference, including the references set forth in the following list:

REFERENCES

1. Rich J N, Eyler C E. Cancer stem cells in brain tumor biology. Cold Spring Harb Symp Quant Biol. 2008; 73:411-20. PMCID: 2822444.
2. Diehn M, Cho R W, Clarke M F. Therapeutic implications of the cancer stem cell hypothesis. Semin Radiat Oncol. 2009; 19(2):78-86.
3. Bao S, Wu Q, McLendon R E, Hao Y, Shi Q, Hjelmeland A B, et al. Glioma stem cells promote radioresistance by preferential activation of the DNA damage response. Nature. 2006; 444(7120):756-60.
4. Sathornsumetee S, Rich J N. Designer therapies for glioblastoma multiforme Ann NY Acad Sci. 2008; 1142:108-32.
5. Park D M, Sathornsumetee S, Rich J N. Medical oncology: treatment and management of malignant gliomas. Nat Rev Clin Oncol. 2010; 7(2):75-7.
6. Venere M, Fine H A, Dirks P B, Rich J N. Cancer stem cells in gliomas: Identifying and understanding the apex cell in cancer's hierarchy. Glia. 2011.
7. Hanahan D, Weinberg R A. The hallmarks of cancer. Cell. 2000; 100(1):57-70.
8. Hanahan D, Weinberg R A. Hallmarks of cancer: the next generation. Cell. 2011; 144(5):646-74.
9. Clarke M F, Dick J E, Dirks P B, Eaves C J, Jamieson C H, Jones D L, et al. Cancer stem cells—perspectives on current status and future directions: AACR Workshop on cancer stem cells. Cancer Res. 2006; 66(19):9339-44.
10. Dick J E. Looking ahead in cancer stem cell research. Nat Biotechnol. 2009; 27(1):44-6.
11. Singh S K, Clarke I D, Terasaki M, Bonn V E, Hawkins C, Squire J, et al. Identification of a cancer stem cell in human brain tumors. Cancer Res. 2003; 63(18):5821-8.
12. Singh S K, Hawkins C, Clarke I D, Squire J A, Bayani J, Hide T, et al. Identification of human brain tumour initiating cells. Nature. 2004; 432(7015):396-401.
13. Bao S, Wu Q, Li Z, Sathornsumetee S, Wang H, McLendon R E, et al. Targeting cancer stem cells through L1CAM suppresses glioma growth. Cancer Res. 2008; 68(15):6043-8.
14. Lathia J D, Gallagher J, Heddleston J M, Wang J, Eyler C E, Macswords J, et al. Integrin alpha 6 regulates glioblastoma stem cells. Cell Stem Cell. 2010; 6(5):421-32. PMCID: 2884275.
15. Son M J, Woolard K, Nam D H, Lee J, Fine H A. SSEA-1 is an enrichment marker for tumor-initiating cells in human glioblastoma. Cell Stem Cell. 2009; 4(5):440-52.

16. Beier D, Wischhusen J, Dietmaier W, Hau P, Proescholdt M, Brawanski A, et al. CD133 expression and cancer stem cells predict prognosis in high-grade oligodendroglial tumors. Brain Pathol. 2008; 18(3):370-7.
17. Raso A, Mascelli S, Biassoni R, Nozza P, Kool M, Pistorio A, et al. High levels of PROM1 (CD 133) transcript are a potential predictor of poor prognosis in medulloblastoma. Neuro Oncol. 2011; 13(5):500-8.
18. Bao S, Wu Q, Sathornsumetee S, Hao Y, Li Z, Hjelmeland A B, et al. Stem cell-like glioma cells promote tumor angiogenesis through vascular endothelial growth factor. Cancer Res. 2006; 66(16):7843-8.
19. Eyler C E, Rich J N. Survival of the fittest: cancer stem cells in therapeutic resistance and angiogenesis. J Clin Oncol. 2008; 26(17):2839-45. PMCID: 2739000.
20. Hambardzumyan D, Squatrito M, Holland E C. Radiation resistance and stem-like cells in brain tumors. Cancer Cell. 2006; 10(6):454-6.
21. Fu J, Liu Z G, Liu X M, Chen F R, Shi H L, Pangjesse C S, et al. Glioblastoma stem cells resistant to temozolomide-induced autophagy. Chin Med J (Engl). 2009; 122(11):1255-9.
22. Liu G, Yuan X, Zeng Z, Tunici P, Ng H, Abdulkadir I R, et al. Analysis of gene expression and chemoresistance of CD133+ cancer stem cells in glioblastoma. Mol Cancer. 2006; 5:67. PMCID: 1697823.
23. Shervington A, Lu C. Expression of multidrug resistance genes in normal and cancer stem cells. Cancer Invest. 2008; 26(5):535-42.
24. Eramo A, Ricci-Vitiani L, Zeuner A, Pallini R, Lotti F, Sette G, et al. Chemotherapy resistance of glioblastoma stem cells. Cell Death Differ. 2006; 13(7):1238-41.
25. Li X, Lewis M T, Huang J, Gutierrez C, Osborne C K, Wu M F, et al. Intrinsic resistance of tumorigenic breast cancer cells to chemotherapy. J Natl Cancer Inst. 2008; 100(9):672-9.
26. Miele L, Miao H, Nickoloff B J. NOTCH signaling as a novel cancer therapeutic target. Curr Cancer Drug Targets. 2006; 6(4):313-23.
27. Pannuti A, Foreman K, Rizzo P, Osipo C, Golde T, Osborne B, et al. Targeting Notch to target cancer stem cells. Clin Cancer Res. 2010; 16(12):3141-52.
28. Bolos V, Grego-Bessa J, de la Pompa J L. Notch signaling in development and cancer. Endocr Rev. 2007; 28(3):339-63.
29. Pierfelice T J, Schreck K C, Eberhart C G, Gaiano N. Notch, neural stem cells, and brain tumors. Cold Spring Harb Symp Quant Biol. 2008; 73:367-75.
30. Stylianou S, Clarke R B, Brennan K. Aberrant activation of notch signaling in human breast cancer. Cancer Res. 2006; 66(3):1517-25.
31. Demarest R M, Ratti F, Capobianco A J. It's T-ALL about Notch. Oncogene. 2008; 27(38):5082-91.
32. Kanamori M, Kawaguchi T, Nigro J M, Feuerstein B G, Berger M S, Miele L, et al. Contribution of Notch signaling activation to human glioblastoma multiforme. J Neurosurg. 2007; 106(3):417-27.
33. Lino M M, Merlo A, Boulay J L. Notch signaling in glioblastoma: a developmental drug target? BMC Med. 2010; 8:72. PMCID: 2996337.
34. Wang J, Wakeman T P, Lathia J D, Hjelmeland A B, Wang X-F, White R R, et al. Notch Promotes Radioresistance of Glioma Stem Cells. Stem Cells. 2010; 28(1):17-28.
35. Gilbert C A, Daou M C, Moser R P, Ross A H. Gamma-secretase inhibitors enhance temozolomide treatment of human gliomas by inhibiting neurosphere repopulation and xenograft recurrence. Cancer Res. 2010; 70(17):6870-9. PMCID: 2932884.
36. Fan X, Khaki L, Zhu T S, Soules M E, Talsma C E, Gul N, et al. NOTCH pathway blockade depletes CD133-positive glioblastoma cells and inhibits growth of tumor neurospheres and xenografts. Stem Cells. 2010; 28(1):5-16.
37. Chen J, Kesari S, Rooney C, Strack P R, Shen H, Wu L, et al Inhibition of Notch Signaling Blocks Growth of Glioblastoma Cell Lines and Tumor Neurospheres. Genes Cancer. 2010; 1(8):822-35. PMCID: 2994256.
38. Fan X, Matsui W, Khaki L, Stearns D, Chun J, Li Y M, et al. Notch pathway inhibition depletes stem-like cells and blocks engraftment in embryonal brain tumors. Cancer Res. 2006; 66(15):7445-52.
39. Appels N M, Beijnen J H, Schellens J H. Development of farnesyl transferase inhibitors: a review. Oncologist. 2005; 10(8):565-78.
40. Lebowitz P F, Prendergast G C. Non-Ras targets of farnesyltransferase inhibitors: focus on Rho. Oncogene. 1998; 17(11 Reviews):1439-45.
41. Liu A, Du W, Liu J P, Jessell T M, Prendergast G C. RhoB alteration is necessary for apoptotic and antineoplastic responses to farnesyltransferase inhibitors. Mol Cell Biol. 2000; 20(16):6105-13. PMCID: 86086.
42. Liu A, Cerniglia G J, Bernhard E J, Prendergast G C. RhoB is required to mediate apoptosis in neoplastically transformed cells after DNA damage. Proc Natl Acad Sci USA. 2001; 98(11):6192-7. PMCID: 33444.
43. Prendergast G C. Actin' up: RhoB in cancer and apoptosis. Nat Rev Cancer. 2001; 1(2):162-8.
44. Jiang K, Coppola D, Crespo N C, Nicosia S V, Hamilton A D, Sebti S M, et al. The phosphoinositide 3-OH kinase/AKT2 pathway as a critical target for farnesyltransferase inhibitor-induced apoptosis. Mol Cell Biol. 2000; 20(1):139-48. PMCID: 85069.
45. Thomas X, Elhamri M. Tipifarnib in the treatment of acute myeloid leukemia. Biologics. 2007; 1(4):415-24. PMCID: 2721284.
46. Harousseau J L, Lancet J E, Reiffers J, Lowenberg B, Thomas X, Huguet F, et al. A phase 2 study of the oral farnesyltransferase inhibitor tipifarnib in patients with refractory or relapsed acute myeloid leukemia. Blood. 2007; 109(12):5151-6.
47. Cloughesy T F, Wen P Y, Robins H I, Chang S M, Groves M D, Fink K L, et al. Phase II trial of tipifarnib in patients with recurrent malignant glioma either receiving or not receiving enzyme-inducing antiepileptic drugs: a North American Brain Tumor Consortium Study. J Clin Oncol. 2006; 24(22):3651-6.
48. Lustig R, Mikkelsen T, Lesser G, Grossman S, Ye X, Desideri S, et al. Phase II preradiation R115777 (tipifarnib) in newly diagnosed GBM with residual enhancing disease. Neuro Oncol. 2008; 10(6):1004-9. PMCID: 2718997.
49. Nghiemphu P L, Wen P Y, Lamborn K R, Drappatz J, Robins H I, Fink K, et al. A Phase I Trial of Tipifarnib with Radiation Therapy, with and without temozolomide, for Patients with Newly Diagnosed Glioblastoma. Int J Radiat Oncol Biol Phys. 2010. PMCID: 3020272.
50. Haas-Kogan D A, Banerjee A, Poussaint T Y, Kocak M, Prados M D, Geyer J R, et al. Phase II trial of tipifarnib and radiation in children with newly diagnosed diffuse intrinsic pontine gliomas. Neuro Oncol. 2011; 13(3):298-306. PMCID: 3064607.

51. Brandes A A, Franceschi E, Tosoni A, Hegi M E, Stupp R. Epidermal growth factor receptor inhibitors in neuro-oncology: hopes and disappointments. Clin Cancer Res. 2008; 14(4):957-60.
52. Riemenschneider M J, Jeuken J W, Wesseling P, Reifenberger G. Molecular diagnostics of gliomas: state of the art. Acta Neuropathol. 2010; 120(5):567-84. PMCID: 2955236.
53. Nutt C L, Mani D R, Betensky R A, Tamayo P, Cairncross J G, Ladd C, et al. Gene expression-based classification of malignant gliomas correlates better with survival than histological classification. Cancer Res. 2003; 63(7):1602-7.
54. Phillips H S, Kharbanda S, Chen R, Forrest W F, Soriano R H, Wu T D, et al. Molecular subclasses of high-grade glioma predict prognosis, delineate a pattern of disease progression, and resemble stages in neurogenesis. Cancer Cell. 2006; 9(3):157-73.
55. Comprehensive genomic characterization defines human glioblastoma genes and core pathways. Nature. 2008; 455 (7216):1061-8. PMCID: 2671642.
56. Li A, Walling J, Ahn S, Kotliarov Y, Su Q, Quezado M, et al. Unsupervised analysis of transcriptomic profiles reveals six glioma subtypes. Cancer Res. 2009; 69(5):2091-9. PMCID: 2845963.
57. Verhaak R G, Hoadley K A, Purdom E, Wang V, Qi Y, Wilkerson M D, et al. Integrated genomic analysis identifies clinically relevant subtypes of glioblastoma characterized by abnormalities in PDGFRA, IDH1, EGFR, and NF1. Cancer Cell. 2010; 17(1):98-110. PMCID: 2818769.
58. Parsons D W, Jones S, Zhang X, Lin J C, Leary R J, Angenendt P, et al. An integrated genomic analysis of human glioblastoma multiforme. Science. 2008; 321(5897):1807-12. PMCID: 2820389.
59. Brennan C, Momota H, Hambardzumyan D, Ozawa T, Tandon A, Pedraza A, et al. Glioblastoma subclasses can be defined by activity among signal transduction pathways and associated genomic alterations. PLoS One. 2009; 4(11):e7752. PMCID: 2771920.
60. Sundaram M V. The love-hate relationship between Ras and Notch. Genes Dev. 2005; 19(16):1825-39.
61. Gutierrez A, Look A T. NOTCH and PI3K-AKT pathways intertwined. Cancer Cell. 2007; 12(5):411-3.
62. Wang J, Wakeman T P, Lathia J D, Hjelmeland A B, Wang X F, White R R, et al. Notch Promotes Radioresistance of Glioma Stem Cells. Stem Cells. 2009.
63. Sade H, Krishna S, Sarin A. The anti-apoptotic effect of Notch-1 requires p56lck-dependent, Akt/PKB-mediated signaling in T cells. J Biol Chem. 2004; 279(4):2937-44.
64. Dougherty M J, Santi M, Brose M S, Ma C, Resnick A C, Sievert A J, et al. Activating mutations in BRAF characterize a spectrum of pediatric low-grade gliomas. Neuro Oncol. 2010. PMCID: 2940652.
65. von Deimling A, Korshunov A, Hartmann C. The next generation of glioma biomarkers: MGMT methylation, BRAF fusions and IDH1 mutations. Brain Pathol. 2011; 21(1):74-87.
66. Chou T C. Drug combination studies and their synergy quantification using the Chou-Talalay method. Cancer Res. 2010; 70(2):440-6.
67. Srougi M C, Burridge K. The nuclear guanine nucleotide exchange factors Ect2 and Net1 regulate RhoB-mediated cell death after DNA damage. PLoS One. 2011; 6(2):e17108. PMCID: 3044157.
68. Chin L, Andersen J N, Futreal P A. Cancer genomics: from discovery science to personalized medicine. Nat Med. 2011; 17(3):297-303.
69. Giannini C, Sarkaria J N, Saito A, Uhm J H, Galanis E, Carlson B L, et al. Patient tumor EGFR and PDGFRA gene amplifications retained in an invasive intracranial xenograft model of glioblastoma multiforme. Neuro Oncol. 2005; 7(2):164-76. PMCID: 1871885.
70. Sarkaria J N, Carlson B L, Schroeder M A, Grogan P, Brown P D, Giannini C, et al. Use of an orthotopic xenograft model for assessing the effect of epidermal growth factor receptor amplification on glioblastoma radiation response. Clin Cancer Res. 2006; 12(7 Pt 1):2264-71.
71. Sarkaria J N, Yang L, Grogan P T, Kitange G J, Carlson B L, Schroeder M A, et al. Identification of molecular characteristics correlated with glioblastoma sensitivity to EGFR kinase inhibition through use of an intracranial xenograft test panel. Mol Cancer Ther. 2007; 6(3):1167-74.
72. Jensen J B, Parmar M. Strengths and limitations of the neurosphere culture system. Mol Neurobiol. 2006; 34(3):153-61.
73. Lee J, Kotliarova S, Kotliarov Y, Li A, Su Q, Donin N M, et al. Tumor stem cells derived from glioblastomas cultured in bFGF and EGF more closely mirror the phenotype and genotype of primary tumors than do serum-cultured cell lines. Cancer Cell. 2006; 9(5):391-403.
74. Weijzen S, Rizzo P, Braid M, Vaishnav R, Jonkheer S M, Zlobin A, et al. Activation of Notch-1 signaling maintains the neoplastic phenotype in human Ras-transformed cells. Nat Med. 2002; 8(9):979-86.
75. Mittal S, Subramanyam D, Dey D, Kumar R V, Rangarajan A. Cooperation of Notch and Ras/MAPK signaling pathways in human breast carcinogenesis. Mol Cancer. 2009; 8:128. PMCID: 2809056.
76. Fitzgerald K, Harrington A, Leder P. Ras pathway signals are required for notch-mediated oncogenesis. Oncogene. 2000; 19(37):4191-8.
77. Chinnaiyan P, Allen G W, Harari P M. Radiation and new molecular agents, part II: targeting HDAC, HSP90, IGF-1R, PI3K, and Ras. Semin Radiat Oncol. 2006; 16(1):59-64.
78. Gupta A K, Bakanauskas V J, Cerniglia G J, Cheng Y, Bernhard E J, Muschel R J, et al. The Ras radiation resistance pathway. Cancer Res. 2001; 61(10):4278-82.
79. Wu Y, Cain-Hom C, Choy L, Hagenbeek T J, de Leon G P, Chen Y, et al. Therapeutic antibody targeting of individual Notch receptors. Nature. 2010; 464(7291):1052-7.
80. Purow B W, Sundaresan T K, Burdick M J, Kefas B A, Comeau L D, Hawkinson M P, et al. Notch-1 regulates transcription of the epidermal growth factor receptor through p53. Carcinogenesis. 2008; 29(5):918-25.
81. Dong Y, Li A, Wang J, Weber J D, Michel L S. Synthetic lethality through combined Notch-epidermal growth factor receptor pathway inhibition in basal-like breast cancer. Cancer Res. 2010; 70(13):5465-74.
82. Aguirre A, Rubio M E, Gallo V. Notch and EGFR pathway interaction regulates neural stem cell number and self-renewal. Nature. 2010; 467(7313):323-7. PMCID: 2941915.
83. Jin S, Hansson E M, Tikka S, Lanner F, Sahlgren C, Farnebo F, et al. Notch signaling regulates platelet-derived growth factor receptor-beta expression in vascular smooth muscle cells. Circ Res. 2008; 102(12):1483-91.
84. Wang J, Wang H, Li Z, Wu Q, Lathia J D, McLendon R E, et al. c-Myc is required for maintenance of glioma cancer stem cells. PLoS ONE. 2008; 3(11):e3769. PMCID: 2582454.

85. Wang H, Lathia J D, Wu Q, Wang J, Li Z, Heddleston J M, et al. Targeting Interleukin 6 Signaling Suppresses Glioma Stem Cell Survival and Tumor Growth. Stem Cells. 2009.
86. Charles N, Ozawa T, Squatrito M, Bleau A M, Brennan C W, Hambardzumyan D, et al. Perivascular nitric oxide activates notch signaling and promotes stem-like character in PDGF-induced glioma cells. Cell Stem Cell. 2010; 6(2): 141-52.
87. Gustafsson M V, Zheng X, Pereira T, Gradin K, Jin S, Lundkvist J, et al. Hypoxia requires notch signaling to maintain the undifferentiated cell state. Dev Cell. 2005; 9(5):617-28.
88. Ishimura N, Bronk S F, Gores G J. Inducible nitric oxide synthase up-regulates Notch-1 in mouse cholangiocytes: implications for carcinogenesis. Gastroenterology. 2005; 128(5):1354-68.
89. Sahlgren C, Gustafsson M V, Jin S, Poellinger L, Lendahl U. Notch signaling mediates hypoxia-induced tumor cell migration and invasion. Proc Natl Acad Sci USA. 2008; 105(17):6392-7. PMCID: 2359811.
90. Liu A X, Rane N, Liu J P, Prendergast G C. RhoB is dispensable for mouse development, but it modifies susceptibility to tumor formation as well as cell adhesion and growth factor signaling in transformed cells. Mol Cell Biol. 2001; 21(20):6906-12. PMCID: 99867.
91. Prendergast G C, Khosravi-Far R, Solski P A, Kurzawa H, Lebowitz P F, Der C J. Critical role of Rho in cell transformation by oncogenic Ras. Oncogene. 1995; 10(12):2289-96.
92. Lebowitz P F, Casey P J, Prendergast G C, Thissen J A. Farnesyltransferase inhibitors alter the prenylation and growth-stimulating function of RhoB. J Biol Chem. 1997; 272(25):15591-4.
93. Delmas C, Heliez C, Cohen-Jonathan E, End D, Bonnet J, Favre G, et al. Farnesyltransferase inhibitor, R115777, reverses the resistance of human glioma cell lines to ionizing radiation. Int J Cancer. 2002; 100(1):43-8.
94. Luistro L, He W, Smith M, Packman K, Vilenchik M, Carvajal D, et al. Preclinical profile of a potent gamma-secretase inhibitor targeting notch signaling with in vivo efficacy and pharmacodynamic properties. Cancer Res. 2009; 69(19):7672-80.
95. Dalenc F, Doisneau-Sixou S F, Allal B C, Marsili S, Lauwers-Cances V, Chaoui K, et al. Tipifarnib plus tamoxifen in tamoxifen-resistant metastatic breast cancer: a negative phase II and screening of potential therapeutic markers by proteomic analysis. Clin Cancer Res. 2010; 16(4):1264-71.
96. Bridges E, Oon C E, Harris A. Notch regulation of tumor angiogenesis. Future Oncol. 2011; 7(4):569-88.
97. Li J L, Harris A L. Notch signaling from tumor cells: a new mechanism of angiogenesis. Cancer Cell. 2005; 8(1):1-3.
98. Cloughesy T F, Kuhn J, Robins H I, Abrey L, Wen P, Fink K, et al. Phase I trial of tipifarnib in patients with recurrent malignant glioma taking enzyme-inducing antiepileptic drugs: a North American Brain Tumor Consortium Study. J Clin Oncol. 2005; 23(27):6647-56.
99. Zimmerman T M, Harlin H, Odenike O M, Berk S, Sprague E, Karrison T, et al. Dose-ranging pharmacodynamic study of tipifarnib (R115777) in patients with relapsed and refractory hematologic malignancies. J Clin Oncol. 2004; 22(23):4816-22.
100. Cook J J, Wildsmith K R, Gilberto D B, Holahan M A, Kinney G G, Mathers P D, et al. Acute gamma-secretase inhibition of nonhuman primate CNS shifts amyloid precursor protein (APP) metabolism from amyloid-beta production to alternative APP fragments without amyloid-beta rebound. J Neurosci. 2010; 30(19):6743-50. PMCID: 2913973.
101. Ying M, Wang S, Sang Y, Sun P, Lal B, Goodwin C R, et al. Regulation of glioblastoma stem cells by retinoic acid: role for Notch pathway inhibition. Oncogene. 2011.
102. Yang L, Clarke M J, Carlson B L, Mladek A C, Schroeder M A, Decker P, et al. PTEN loss does not predict for response to RAD001 (Everolimus) in a glioblastoma orthotopic xenograft test panel. Clin Cancer Res. 2008; 14(12):3993-4001.
103. Carlson B L, Grogan P T, Mladek A C, Schroeder M A, Kitange G J, Decker P A, et al. Radiosensitizing effects of temozolomide observed in vivo only in a subset of O6-methylguanine-DNA methyltransferase methylated glioblastoma multiforme xenografts. Int J Radiat Oncol Biol Phys. 2009; 75(1):212-9. PMCID: 2773462.
104. Hodgson J G, Yeh R F, Ray A, Wang N J, Smirnov I, Yu M, et al. Comparative analyses of gene copy number and mRNA expression in glioblastoma multiforme tumors and xenografts. Neuro Oncol. 2009; 11(5):477-87. PMCID: 2765338.
105. Esteller M, Garcia-Foncillas J, Andion E, Goodman S N, Hidalgo O F, Vanaclocha V, et al. Inactivation of the DNA-repair gene MGMT and the clinical response of gliomas to alkylating agents. N Engl J Med. 2000; 343(19):1350-4.
106. Stupp R, Hegi M E, Mason W P, van den Bent M J, Taphoorn M J, Janzer R C, et al. Effects of radiotherapy with concomitant and adjuvant temozolomide versus radiotherapy alone on survival in glioblastoma in a randomised phase III study: 5-year analysis of the EORTC-NCIC trial. Lancet Oncol. 2009; 10(5):459-66.
107. Tibshirani R. Regression Shrinkage and Selection via the Lasso. Journal of the Royal Statistical Society Series B (Methodological). 1996; 58(1):267-88.
108. Obuchowski N A, McClish D K. Sample size determination for diagnostic accuracy studies involving binormal ROC curve indices. Stat Med. 1997; 16(13):1529-42.
109. Friedman J, Hastie T, Tibshirani R. Regularization Paths for Generalized Linear Models via Coordinate Descent. J Stat Softw. 2010; 33(1):1-22. PMCID: 2929880.
110. Holzel M, Rohrmoser M, Orban M, Homig C, Harasim T, Malamoussi A, et al. Rapid conditional knock-down-knock-in system for mammalian cells. Nucleic Acids Res. 2007; 35(3):e17. PMCID: 1807947.
111. Tolcher A W, Messersmith W A, Mikulski S M, Papadopoulos K P, Kwak E L, Gibbon D G, et al. Phase I Study of RO4929097, a Gamma Secretase Inhibitor of Notch Signaling, in Patients With Refractory Metastatic or Locally Advanced Solid Tumors. J Clin Oncol. 2012.
112. Adjei A A, Davis J N, Erlichman C, Svingen P A, Kaufmann S H. Comparison of potential markers of farnesyltransferase inhibition. Clin Cancer Res. 2000; 6:2318-25.
113. Mukherjee T, Kim W S, Mandal L, Banerjee U. Interaction between Notch and Hif-alpha in development and survival of *Drosophila* blood cells. Science. 2011; 332: 1210-3.
114. Qiang L, Wu T, Zhang H W, Lu N, Hu R, Wang Y J, et al. HIF-1alpha is critical for hypoxia-mediated maintenance of glioblastoma stem cells by activating Notch signaling pathway. Cell Death Differ. 2012; 19:284-94.
115. Mazumdar J, Dondeti V, Simon M C. Hypoxia-inducible factors in stem cells and cancer. J Cell Mol Med. 2009; 13:4319-28.
116. Melillo G. Targeting hypoxia cell signaling for cancer therapy. Cancer Metastasis Rev. 2007; 26:341-52.

117. Li Z, Rich J N. Hypoxia and hypoxia inducible factors in cancer stem cell maintenance. Curr Top Microbiol Immunol. 2010; 345:21-30.
118. Wilson W R, Hay M P. Targeting hypoxia in cancer therapy. Nat Rev Cancer. 2011; 11:393-410.
119. Carlson B L, Pokorny J L, Schroeder M A, Sarkaria J N. Establishment, maintenance and in vitro and in vivo applications of primary human glioblastoma multiforme (GBM) xenograft models for translational biology studies and drug discovery. Curr Protoc Pharmacol. 2011; Chapter 14:Unit 14 6.
120. Reynolds B A, Weiss S. Generation of neurons and astrocytes from isolated cells of the adult mammalian central nervous system. Science. 1992; 255:1707-10.

What is claimed is:

1. A composition, comprising:
 a farnesyl transferase inhibitor (FTI); and
 a gamma-secretase inhibitor (GSI).
2. The composition of claim 1, wherein the FTI is selected from tipifarnib, lonafarnib, and L744,832.
3. The composition of claim 2, wherein the GSI is selected from RO4929097, DAPT, compound E, MK-0752, and PF03084014.
4. The composition of claim 1, wherein the GSI is selected from RO4929097, DAPT, compound E, MK-0752, and PF03084014.
5. The composition of claim 1, wherein the FTI is tipifarnib.
6. The composition of claim 1, wherein the FTI is L744,832.
7. The composition of claim 1, wherein the GSI is RO4929097.
8. The composition of claim 1, wherein the GSI is DAPT.
9. The composition of claim 1, wherein the GSI is compound E.
10. The composition of claim 1, wherein the FTI is tipifarnib and the GSI is RO4929097.
11. The composition of claim 1, wherein the FTI is L744,832 and the GSI is DAPT.
12. The composition of claim 1, and further comprising an EGFR inhibitors, an insulin receptor, or an IGF-1R inhibitor.
13. The composition of claim 1, wherein the composition is provided for the treatment of glioblastoma multiforme (GBM).
14. The composition of claim 1, wherein the FTI and GSI produce an effect against glioblastoma cells.
15. The composition of claim 14, wherein the effect against glioblastoma cells is selected from an inhibition in the growth of glioblastoma cells, a killing of glioblastoma cells, and a reduction in symptoms associated with the presence of glioblastoma cells.
16. The composition of claim 1, wherein the FTI and the GSI produce a synergistic effect against glioblastoma cells.
17. The composition of claim 1, wherein the FTI and GSI are provided in a ratio selected from about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, and 1:20 (wt/wt).
18. A method of targeting a glioblastoma cell, comprising:
 contacting a glioblastoma cell with a composition, comprising
 a farnesyl transferase inhibitor (FTI); and
 a gamma-secretase inhibitor (GSI).
19. The method of claim 18, wherein contacting the cell with the composition produces an effect against glioblastoma cells is selected from an inhibition in the growth of glioblastoma cells, a killing of glioblastoma cells, and a reduction in symptoms associated with the presence of glioblastoma cells.
20. The method of claim 18, wherein the contacting a glioblastoma cell with the composition comprises administering the composition to a subject.
21. The method of claim 18, wherein the FTI and the GSI produce a synergistic effect against the glioblastoma cell.
22. The method of claim 21, wherein the effect against glioblastoma cells is selected from an inhibition in the growth of glioblastoma cells, a killing of glioblastoma cells, and a reduction in symptoms associated with the presence of glioblastoma cells.
23. The method of claim 18, and further comprising administering radiation to the subject.
24. The composition of claim 1, wherein the FTI is tipifarnib and the GSI is MK-0752.

* * * * *